United States Patent
Dresser et al.

(10) Patent No.: US 11,278,351 B2
(45) Date of Patent: Mar. 22, 2022

(54) DIFFRACTIVE OPTICS FOR EMR-BASED TISSUE TREATMENT

(71) Applicant: Avava, Inc., Boston, MA (US)

(72) Inventors: Charles Holland Dresser, Wayland, MA (US); Rajender Katkam, Boston, MA (US); Jayant Bhawalkar, Auburndale, MA (US)

(73) Assignee: Avava, Inc., Boston, MA (US)

( * ) Notice: Subject to any disclaimer, the term of this patent is extended or adjusted under 35 U.S.C. 154(b) by 83 days.

(21) Appl. No.: 16/381,736

(22) Filed: Apr. 11, 2019

(65) Prior Publication Data

US 2019/0314085 A1 Oct. 17, 2019

Related U.S. Application Data

(60) Provisional application No. 62/688,913, filed on Jun. 22, 2018, provisional application No. 62/656,639, filed on Apr. 12, 2018.

(51) Int. Cl.
*A61B 18/20* (2006.01)
*A61B 18/22* (2006.01)
*A61B 18/00* (2006.01)

(52) U.S. Cl.
CPC .......... *A61B 18/203* (2013.01); *A61B 18/201* (2013.01); *A61B 18/22* (2013.01); *A61B 2018/00452* (2013.01); *A61B 2018/00577* (2013.01); *A61B 2018/00636* (2013.01)

(58) Field of Classification Search
CPC ..... A61B 18/203; A61B 18/201; A61B 18/22; A61B 2018/00452; A61B 2018/00577; A61B 2018/00636
See application file for complete search history.

(56) References Cited

U.S. PATENT DOCUMENTS

| | | | |
|---|---|---|---|
| 5,312,396 A | 5/1994 | Feld et al. | |
| 2001/0016732 A1 | 8/2001 | Hobart et al. | |
| 2006/0103905 A1 | 5/2006 | Walmsley | |
| 2007/0295817 A1* | 12/2007 | Massieu | G06K 7/10702 235/462.23 |
| 2008/0015557 A1 | 1/2008 | Chan et al. | |
| 2010/0082019 A1* | 4/2010 | Neev | A61B 18/203 606/9 |
| 2011/0196350 A1 | 8/2011 | Friedman et al. | |
| 2017/0112574 A1* | 4/2017 | Cohen | A61B 18/22 |
| 2017/0280970 A1 | 10/2017 | Sartor et al. | |

OTHER PUBLICATIONS

International Search Report and Written Opinion issued in corresponding International Application No. PCT/US2019/027007, dated Aug. 9, 2019, 16 pages.

* cited by examiner

*Primary Examiner* — Michael W Kahelin
(74) *Attorney, Agent, or Firm* — Mintz Levin Cohn Ferris Glovsky and Popeo, P.C.

(57) ABSTRACT

A method includes generating a plurality of primary beams from a laser beam, and generating, from a primary beam one or more secondary beams. The method also includes focusing the first secondary beam to a first focal region in the target tissue and the second secondary beam to a second focal region in the target tissue. The first focal region and the second focal region can be located at different depths in the target tissue.

19 Claims, 35 Drawing Sheets

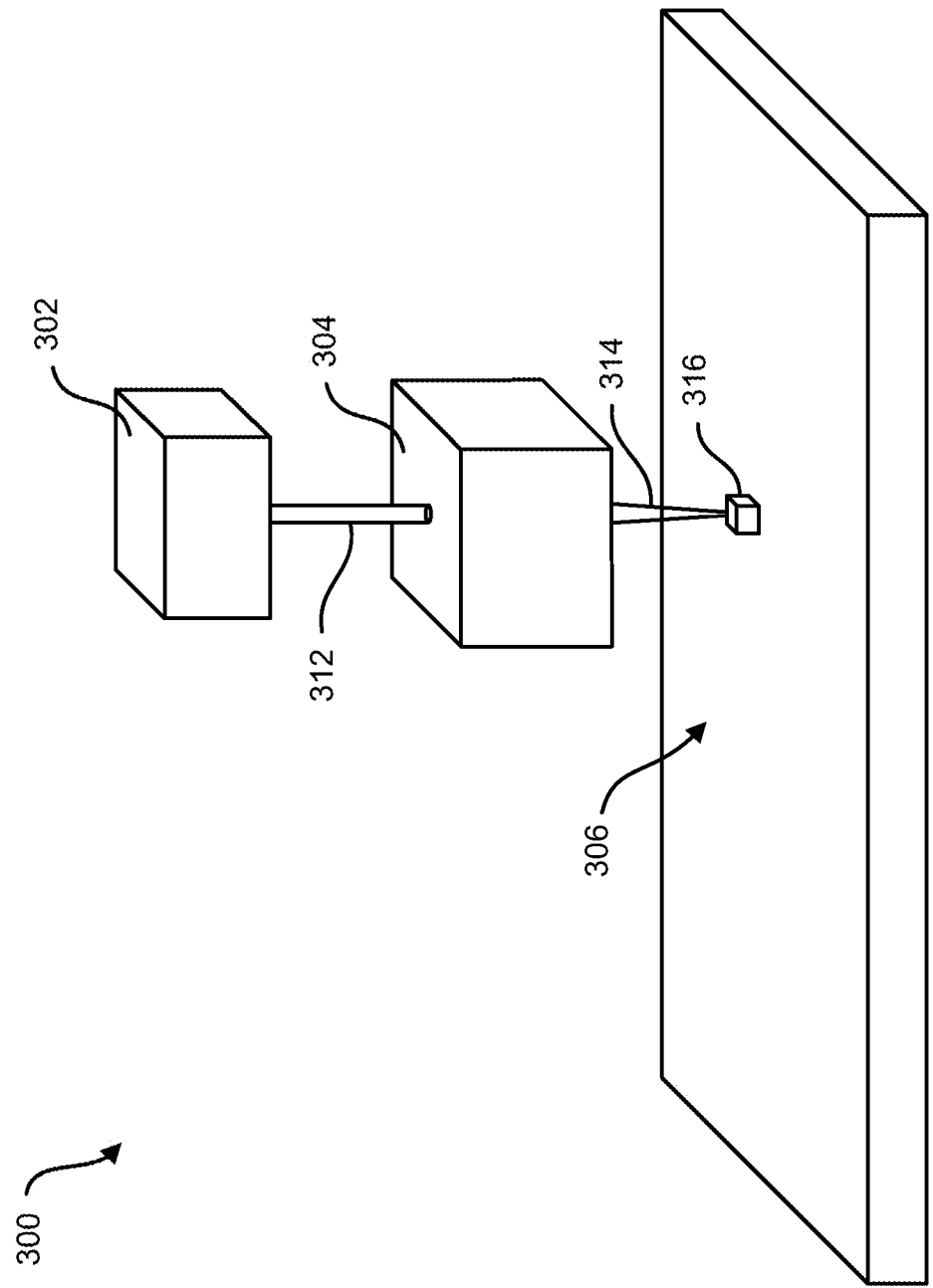

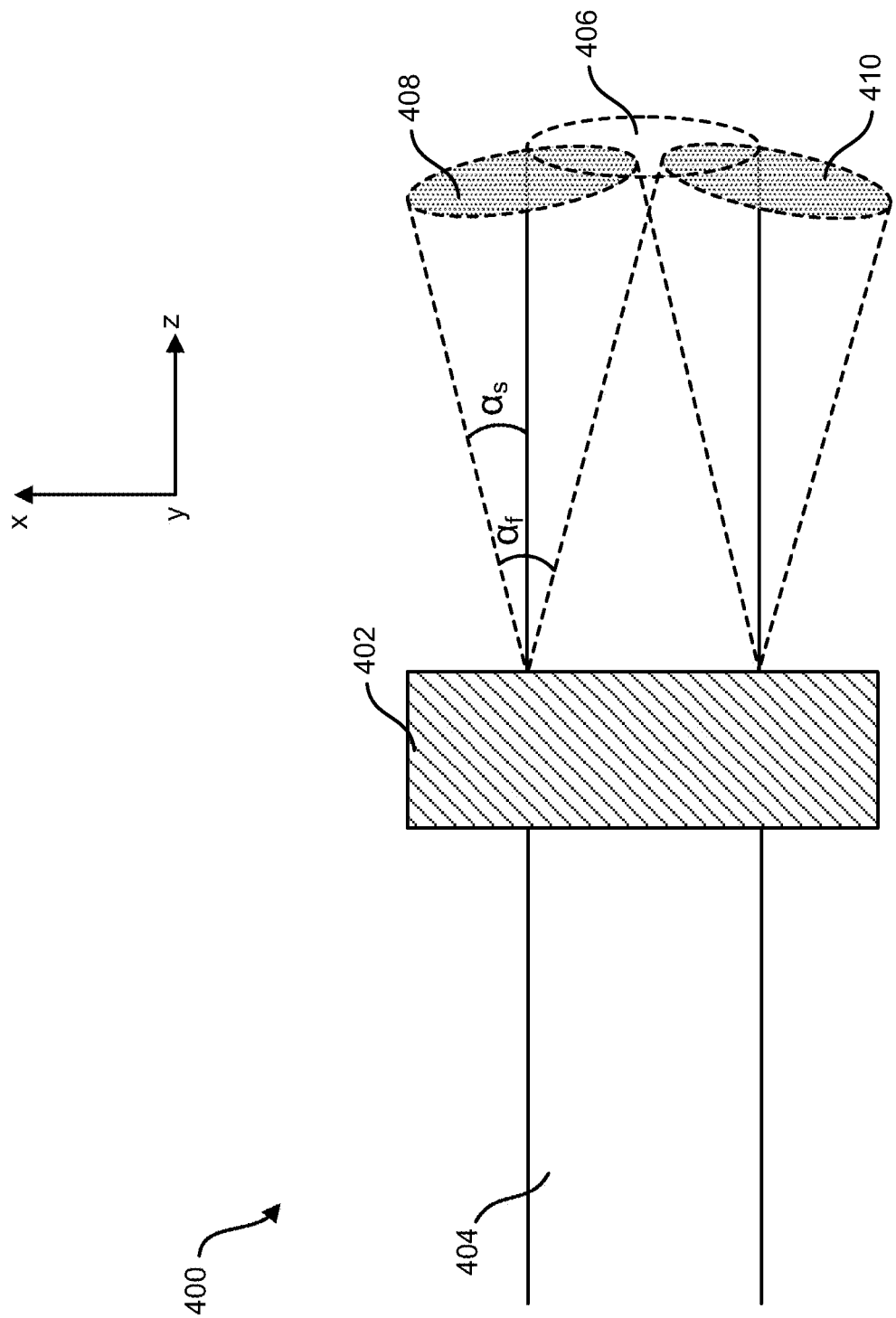

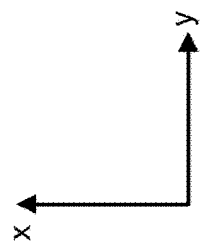
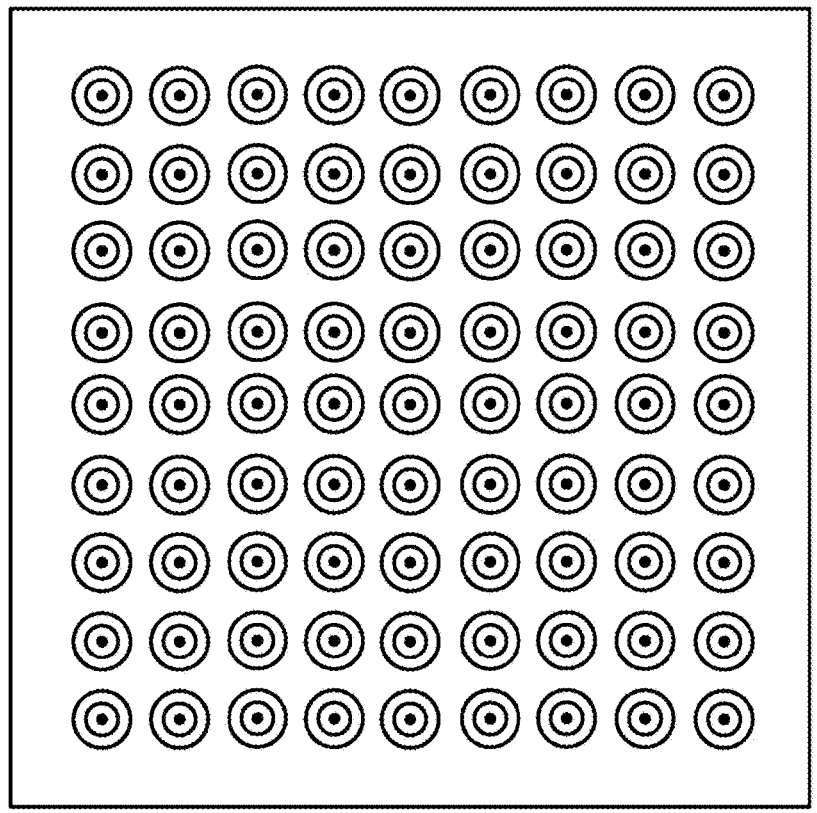
FIG. 4B

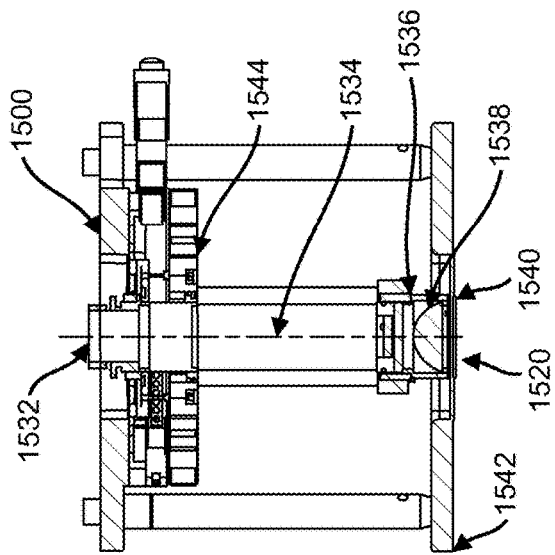
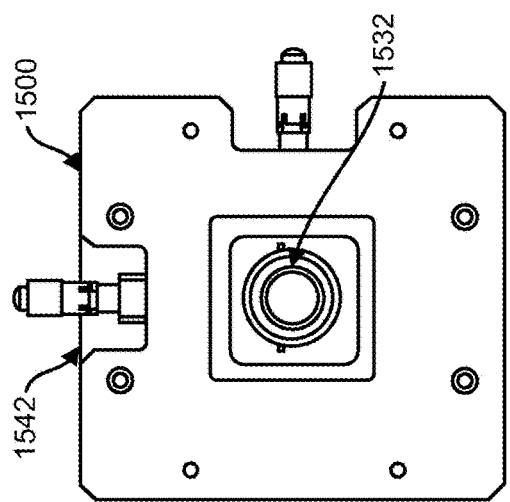
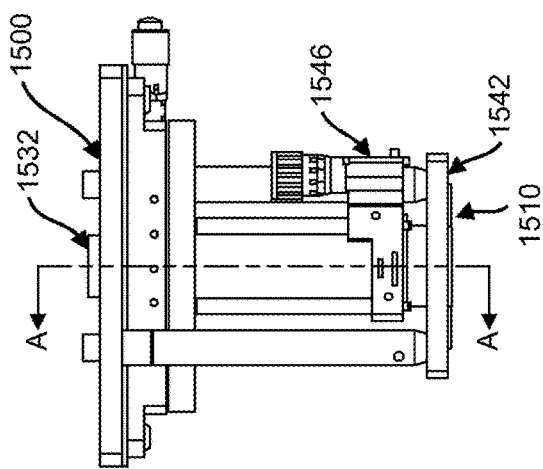
FIG. 15B
FIG. 15C
FIG. 15A

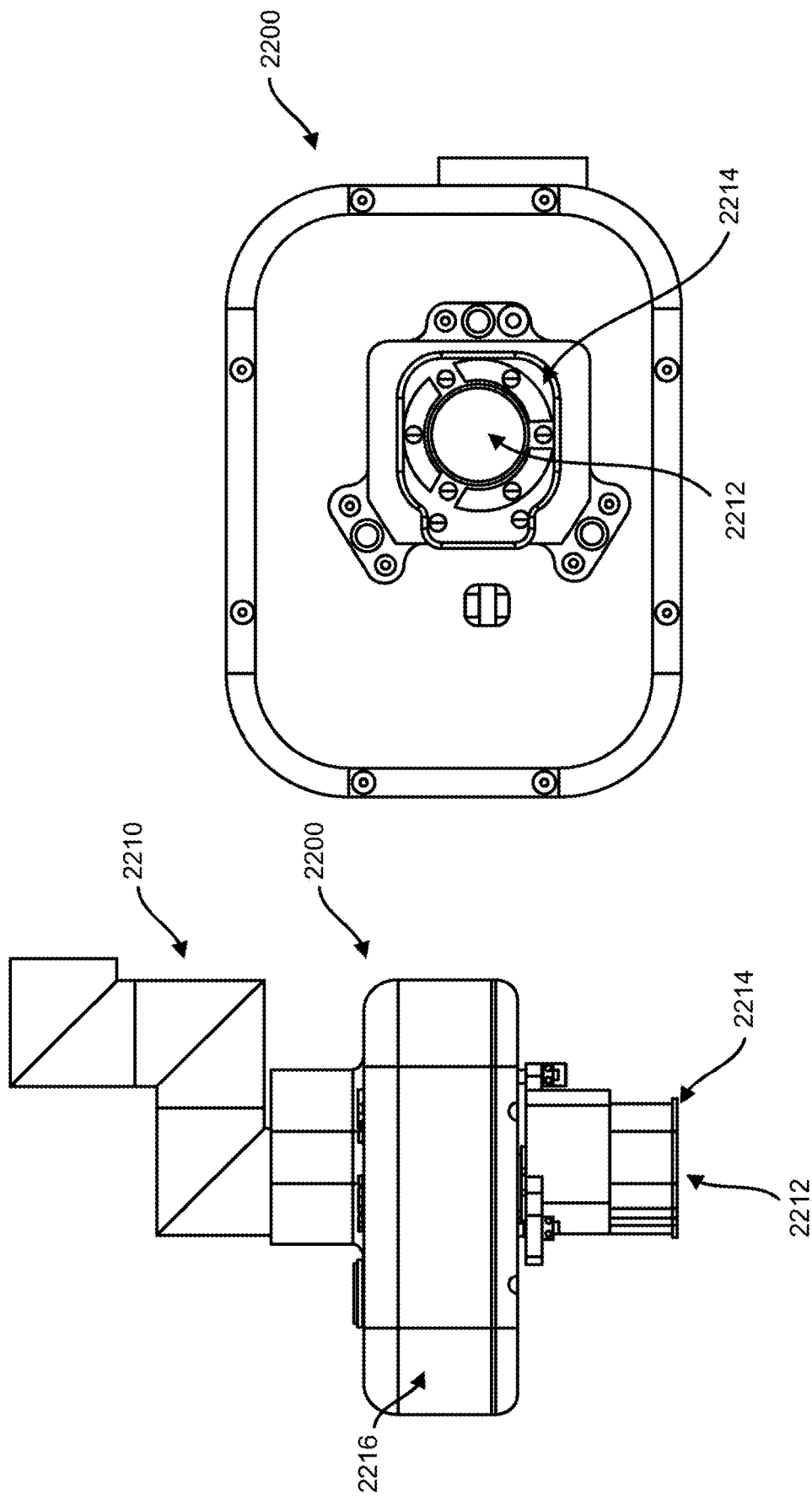

DIFFRACTIVE OPTICS FOR EMR-BASED TISSUE TREATMENT

RELATED APPLICATION

This application claims priority under 35 U.S.C. § 119(e) to U.S. Provisional Patent Application No. 62/656,639 filed on Apr. 12, 2018, and to U.S. Provisional Patent Application No. 62/688,913 filed on Jun. 22, 2018, the entire contents of each of which are hereby expressly incorporated by reference herein.

FIELD

The present disclosure relates generally to methods, systems, and devices for laser-based target tissue treatment.

BACKGROUND

Various conditions can be treated with the application of light or optical energy of certain wavelengths. Many challenges exist in delivering the energy to the appropriate target structure (e.g., tissue such as the skin) without damaging tissue structures adjacent to the target structure. These challenges include delivery of energy at an appropriate wavelength with sufficient fluence and focus as well as the ability to effectively and efficiently scan the target structure with the light or optical energy.

Melasma is an example of one skin disorder of unknown etiology that causes a blotchy hyperpigmentation, often in the facial area. This condition is more common in women than in men. Although the specific cause(s) of melasma may not be well-understood, the pigmented appearance of melasma can be aggravated by certain conditions such as pregnancy, sun exposure, certain medications, such as, e.g., oral contraceptives, hormonal levels, genetics, etc. Exemplary symptoms of melasma include dark, irregularly-shaped patches or macules, which are commonly found on the upper cheek, nose, upper lip, and forehead. These patches often develop gradually over time. Melasma does not appear to cause any other symptoms, nor have other detrimental effects, beyond the cosmetic discoloration.

Unlike many pigmented structures that are typically present in the epidermal region of skin (i.e., at or near the tissue surface), dermal (or deep) melasma is often characterized by widespread presence of melanin and melanophages (including, e.g., excessively-pigmented cells) in portions or regions of the underlying dermis. Accordingly, treatment of dermal melasma (e.g., lightening of the appearance of darkened pigmented regions) can be particularly challenging because of the presence of the greater difficulty in accessing and affecting such pigmented cells and structures located deeper within the skin. Accordingly, conventional skin rejuvenation treatments such as facial peels (laser or chemical), dermabrasion, topical agents, and the like, which primarily affect the overlying epidermis, may not be effective in treating dermal melasma.

SUMMARY

It has been observed that application of light or optical energy of certain wavelengths can be strongly absorbed by pigmented cells, thereby damaging them. However, an effective treatment of pigmentary conditions of the skin, such as dermal melasma or other non-pigmentary conditions, using optical energy introduces several obstacles. For example, pigmented cells in the dermis must be targeted with sufficient optical energy of appropriate wavelength(s) to disrupt or damage them, which may release or destroy some of the pigmentation and reduce the pigmented appearance. However, such energy can be absorbed by pigment (e.g., chromophores) in the overlying skin tissue, such as the epidermis and upper dermis. This near-surface absorption can lead to excessive damage of the outer portion of the skin, and insufficient delivery of energy to the deeper dermis to affect the pigmented cells therein. Moreover, thermal injury to melanocytes located in the basal layer of the epidermis can trigger an increase in the production of melanin resulting in hyperpigmentation and thermal destruction of melanocytes can result in loss of melanin resulting in hypopigmentation.

Fractional approaches have been developed that involve application of optical energy to small, discrete treatment locations on the skin that are separated by healthy tissue to facilitate healing. Accurately targeting the treatment locations (e.g., located in dermal layer) with desirable specificity while avoiding damage to healthy tissue around the treatment location (e.g., in the epidermal layer) can be challenging. This requires, for example, an optical system with high numerical aperture (NA) for focusing a laser beam to a treatment location. Additionally, the optical system should be able to scan the focused beam over large affected regions (e.g., several square centimeters). Therefore, it is desirable to develop an optical system that has a high numerical aperture and be capable of scanning over large affected regions. Further, it is desirable that the optical system be effective to treat the affected region in a reasonable time duration (e.g., less than an hour). Furthermore, it is desirable that the optical system include an interface that can, for example, establish a robust contact with the treatment region, stabilize the treatment region, cool the treatment region, and the like.

Accordingly, improved methods, systems, and devices for electromagnetic radiation (EMR)-based tissue treatment (e.g., laser-based treatment) are provided.

A method includes generating a plurality of primary beams from a laser beam, and generating, from at least a first primary beam of the plurality of primary beams, a first secondary beam and a second secondary beam. The method also includes focusing the first secondary beam to a first focal region in the target tissue and the second secondary beam to a second focal region in the target tissue. The first focal region is located at a first depth from a surface of the target tissue, and the second focal region is located at a second depth different from the first depth of the surface of the target tissue.

In one implementation, the first secondary beam is configured to generate a first plasma in the first focal region and the second secondary beam is configured to generate a second plasma in the second focal region. In another implementation, the first secondary beam and the second secondary beam are generated by a first Fresnel zone plate in an array of Fresnel zone plates. In yet another implementation, the first focal region extends from the first depth to the second depth. In one implementation, the method further includes generating from a second primary beam of the plurality of primary beams, a third secondary beam and a fourth secondary beam, and focusing the third secondary beam to a third focal region and the fourth secondary beam to a fourth focal region in the target tissue.

In one implementation, the third secondary beam is configured to generate plasma in the third focal region and the fourth secondary beam is configured to generate plasma in the fourth focal region. In another implementation, the method further includes distorting the surface of the target tissue to locate the third focal region at the first depth from the surface of the target tissue and the fourth focal region at the second depth from the surface of the target tissue. In yet another implementation, the first and the second secondary beams are focused by a first lens of a multi-lens array, and the third and the fourth secondary beams are focused by a second lens of the multi-lens array.

In one implementation, the first, the second, the third and the fourth secondary beams are focused by an objective. In another implementation, a first diffractive optical element is configured to receive the laser beam and generate the plurality of primary beams. In yet another implementation, the first diffractive optical element is a diffractive beam splitter.

In one implementation, an optical element having numerical aperture between about 0.3 and about 1 focuses the first secondary beam to the first focal region. In another implementation, the generated first plasma is configured to produce a thermal damage at the first focal region in the target tissue, the thermal damage extending from about the first depth to about the second depth. In yet another implementation, the first secondary beam is configured to selectively generate plasma in a volume that includes a target in the quasi-diffraction-free focal region.

A method includes generating, by a laser source, a laser beam including a characteristic wavelength. The method also includes generating, from the laser beam, one or more beamlets. The method further includes focusing, by a first focusing optical element having a first numerical aperture, a first beamlet of the one or more beamlets to a focal volume beneath a tissue surface. The focal volume has an elongated length that extends from a first depth to a second depth in the tissue, and an intensity of the first beamlet is above a predetermined therapeutic threshold in the focal volume.

In one implementation, the elongated length is greater than twice a Rayleigh length for a Gaussian beam centered at the characteristic wavelength and focused by an optical element having the first numerical aperture. In another implementation, the elongated length is greater than:

$$\frac{2\lambda}{\pi N A^2}$$

where $\lambda$ is the characteristic wavelength and NA is the numerical aperture.

In one implementation, the method further includes focusing, by the first optical element, a second beamlet of the one or more beamlets to the focal volume. The focal volume includes a first focal region associated with the first beamlet and a second focal region associated with the second beamlet.

In one implementation, the first beamlet is a quasi-diffraction-free-beam and the focal volume includes a quasi-diffraction-free focal region associated with the first beamlet. In another implementation, the focal volume is beneath a dermis-epidermis junction. In yet another implementation, the method further includes pulsing the laser beam at a pulse duration less than 1000 nanoseconds.

In one implementation, the predetermined therapeutic threshold corresponds to at least one of a minimum intensity required to generate a plasma in the tissue, a minimum intensity required to selectively generate a plasma in a target material in the tissue, and a minimum intensity required to generate thermal damage in the tissue. In another implementation, the first focusing optical element comprises at least one of a diffractive optical element and an axicon. In yet another implementation, the characteristic wavelength ranges from about 0.5 micrometers to about 2 micrometers.

A system includes a diffractive beam splitter configured to receive a laser beam and produce a plurality of primary beams. The system also includes a diffractive element located down-beam from the diffractive beam splitter. The diffractive element is configured to receive at least a first primary beam of the plurality of primary beams and generate at least a first secondary beam and a second secondary beam. The system further includes a focusing element located down-beam from the diffractive element. The diffractive element can be configured to focus the first secondary beam to a first focal region in a target tissue and focus the second secondary beam to a second focal region in the target tissue. The first focal region is located at a first depth from a surface of the target tissue, and the second focal region is located at a second depth different from the first depth of the surface of the target tissue.

In one implementation, the first secondary beam and the second secondary beam are generated by a first Fresnel zone plate in an array of Fresnel zone plates. In another implementation, the diffractive element is configured to receive a second primary beam of the plurality of primary beams and generate at least a third secondary beam and a fourth secondary beam. The diffractive element is also configured to focus the third secondary beam to a third focal region and the fourth secondary beam to a fourth focal region in the target tissue. In yet another implementation, the third secondary beam is configured to generate plasma in the third focal region and the fourth secondary beam is configured to generate plasma in the fourth focal region.

In one implementation, the second secondary beams are focused by a first lens of a multi-lens array, and the third and the fourth secondary beams are focused by a second lens of the multi-lens array. In another implementation, the system further includes a diffractive element configured to receive a laser beam including a characteristic wavelength and separate the laser beam into one or more beamlets having the single wavelength. The system also includes a focusing optical element located down-beam from the diffractive element and having a first numerical aperture. The focusing optical element is configured to focus a first beamlet of the one or more beamlets to a focal volume beneath a tissue surface. The focal volume has an elongated length that extends from a first depth to a second depth in the tissue, and an intensity of the first beamlet is above a predetermined therapeutic threshold in the focal volume.

A system includes an articulating arm configured to receive from a laser source a laser beam at a first end and deliver the laser beam out of a second end. The system also includes a diffractive beam splitter located down-beam from the second end of the articulating arm. The diffractive beam splitter is configured to split the laser beam into a plurality of beams. The system further includes a focusing optical element located down-beam from the diffractive beam splitter. The focusing optical element is configured to focus the plurality of beams to an array of focuses. The system also includes a window located down-beam from the focusing optical element and up-beam from the array of focuses. The window is configured to contact a target tissue and transmit the plurality of beams. The system further includes a first stage configured to translate the second end of the articulating arm, the diffractive beam splitter, and the focusing optical element relative the window in a first direction that is generally perpendicular to an optical axis associated with the plurality of beams.

In one implementation, the system further includes a laser source configured to generate the laser beam at a repetition rate. In another implementation, the system further includes a controller configured to control the translation by the first stage based on at least one of the repetition rate of the laser beam and an array width of the array of focuses. In yet another implementation, the controller is further configured to control at least one of a pulse energy of the laser beam, a pulse duration of the laser beam, and a wavelength of the laser beam to cause generation of thermionic plasma at the array of focuses in pigmented targets within the target tissue. In one implementation, the focusing optical element has a numerical aperture ranging from about 0.3 to about 1.

In one implementation, the system further includes a second stage configured to translate the second end of the articulating arm, the diffractive beam splitter, and the focusing optical element relative the window in a second direction that is generally perpendicular to the optical axis associated with the plurality of beams. In another implementation, the system further includes a third stage configured to translate the focusing optical element in a third direction that is generally parallel to the optical axis associated with the plurality of beams, causing a change in an average distance between the array of focuses and the window. In yet another implementation, the array of focuses include a first focal region and a second focal region. The first focal region is located at a first depth from a surface of the target tissue, and the second focal region is located at a second depth different from the first depth of the surface of the target tissue.

A method includes receiving, by an articulating arm at a first end, a laser beam. The method also includes delivering, by a second end of the articulating arm, the laser beam. The method further includes splitting, by a diffractive beam splitter located down-beam from the second end of the articulating arm, the laser beam into a plurality of beams. The method also includes focusing, by a focusing optical element located down-beam from the diffractive beam splitter, the plurality of beams to an array of focuses. The method further includes transmitting the plurality of beams through a window configured to contact a target tissue. The method also includes translating, by a first stage, the second end of the articulating arm, the diffractive beam splitter, and the focusing optical element relative the window in a first direction that is generally perpendicular to an optical axis associated with the plurality of beams.

In one implementation, the method further includes comprising generating the laser beam at a repetition rate. In another implementation, the method further includes controlling the first stage in response to at least one of the repetition rate of the laser beam and an array width of the array of focuses. In yet another implementation, the method further includes controlling at least one of a pulse energy of the laser beam, a pulse duration of the laser beam, and a wavelength of the laser beam to cause thermionic plasma at the array of focuses in pigmented targets within the target tissue.

In one implementation, focusing the plurality of beams to the array of focuses is done at a numerical aperture ranging from about 0.3 to about 1. In another implementation, the method further includes translating, with a second stage, the second end of the articulating arm, the diffractive beam splitter, and the focusing optical element relative the window in a second direction that is generally perpendicular to the optical axis associated with the plurality of beams. In yet another implementation, the method further includes translating, with a third stage, the focusing optical element in a third direction that is generally parallel to the optical axis associated with the plurality of beams, causing a change in an average distance between the array of focuses and the window. In one implementation, the array of focuses includes a first focal region and a second focal region. The first focal region is located at a first depth from a surface of the target tissue, and the second focal region is located at a second depth different from the first depth of the surface of the target tissue.

A method includes generating a laser beam, and generating, from the laser beam, a first secondary beam and a second secondary beam. The method also includes focusing the first secondary beam to a first focal region in a target tissue and the second secondary beam to a second focal region in the target tissue. The target tissue includes a first tissue layer proximal to a surface of the tissue and a second tissue layer beneath the first tissue layer and the first focal region and the second focal region are located within the second tissue layer. The method also includes controlling, using a controller, at least one laser beam parameter to introduce a therapeutic effect within the first focal region and the second focal region without introducing a deleterious effect within the first tissue layer.

BRIEF DESCRIPTION OF DRAWINGS

Embodiments of the disclosure will be more fully understood from the following detailed description taken in conjunction with the accompanying drawings, in which:

FIG. 3 is a schematic illustration of a tissue treatment system;

FIG. 4A is a schematic illustration of a diffractive optical setup including a diffractive beam splitter;

FIG. 4B is a schematic illustration of an exemplary embodiment of a two-dimensional beam matrix generated by two-dimensional diffraction of a laser beam;

FIG. 15A is an illustration of a first side view of an exemplary test handpiece 1500;

FIG. 15B is an illustration of a second side view of the exemplary optical system in FIG. 15A;

FIG. 15C is an illustration of a top view of the exemplary optical system in FIG. 15A;

FIG. 22A illustrates a front view of an exemplary treatment system handpiece;

FIG. 22B illustrates a bottom view of the exemplary treatment system handpiece in FIG. 22A;

Figure 1:
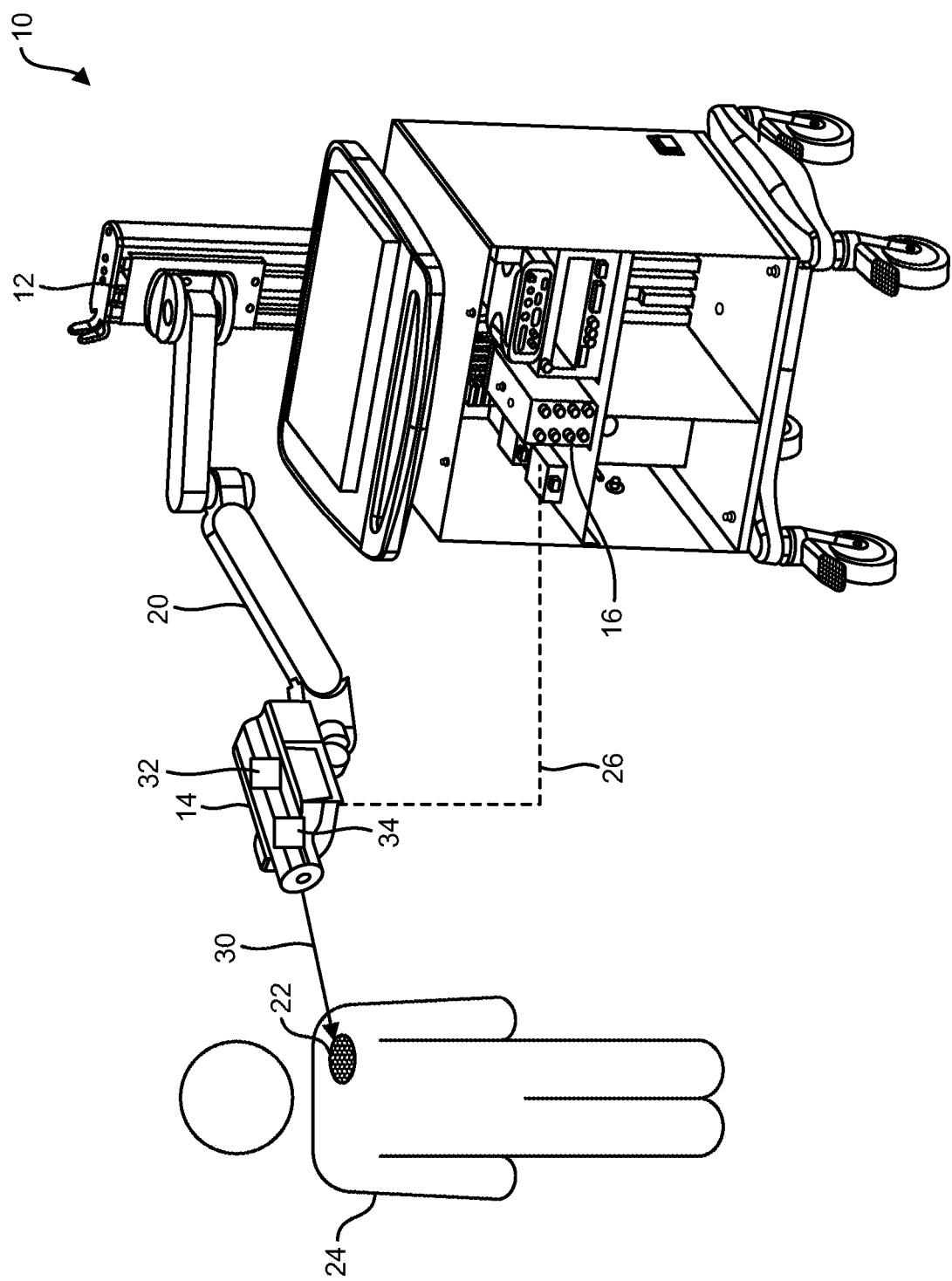
FIG. 1 illustrates an exemplary embodiment of a treatment system.

It is noted that the drawings are not necessarily to scale. The drawings are intended to depict only typical aspects of the subject matter disclosed herein, and therefore should not be considered as limiting the scope of the disclosure. Those skilled in the art will understand that the systems, devices, and methods specifically described herein and illustrated in the accompanying drawings are non-limiting exemplary embodiments and that the scope of the present invention is defined solely by the claims.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Embodiments of the disclosure are discussed in detail below with respect to treatment of pigmentary conditions of the skin, such as melasma, to improve the appearance of such a pigmentary condition. However, the disclosed embodiments can be employed for treatment of other pigmentary and non-pigmentary conditions and other tissue and non-tissue targets without limit. Examples of pigmentary conditions can include, but are not limited to, post inflammatory hyperpigmentation, dark skin surrounding eyes, dark eyes, café au lait patches, Becker's nevi, Nevus of Ota, congenital melanocytic nevi, freckles/lentigo, hemosiderin containing structures, pigmented gallstones, lutein, zeaxanthin, rhodopsin, carotenoid, biliverdin, bilirubin and hemoglobin containing structures, and tattoo-containing tissue. Examples of non-pigmentary conditions can include, but are not limited to, hair follicles, hair shaft, vascular lesions, infectious conditions, sebaceous glands, acne, and the like.

Additionally, remodeling of structures in the skin such as collagen, elastin, and other components of the extra cellular matrix can be envisioned. Examples of such treatments include skin resurfacing, changing the appearance of striae, cellulite, scars, wrinkles, and fine lines, tightening of the skin, changing the texture of the skin, and the like.

Uses of the methods and systems disclosed when applied therapeutically in these ways can result in an improved cosmetic appearance of the skin.

In many instances a therapeutic effect is achieved by disrupting or denaturing a tissue. For example, the therapeutic effect of breaking down a pigment aids in clearing many pigmentary conditions. As another example, a therapeutic effect is achieved in treatment of non-pigmentary conditions, such as rejuvenation through the disruption of normal tissue, which is then replaced by the body with new tissue rejuvenating the appearance of the tissue. Often the therapeutic effect is desired at a specific location (e.g., depth or layer) within the tissue. In some cases, the therapeutic effect is selectively applied to certain types of tissue (e.g., dermal pigment).

During treatment it is important to avoid a deleterious effect in non-targeted tissue. In many cases the deleterious effect is identical to the therapeutic effect, except that it is manifested in an un-targeted region (e.g., layer) of the tissue. For example, deleterious effects include disruption, damage, denaturing, and ablation of the tissue.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, high numerical aperture (NA) optical systems are described that can focus electromagnetic radiation (EMR) (e.g., a laser beam) to a treatment region in a tissue. The focused laser beam can deliver optical energy to the treatment region without harming the surrounding tissue. The delivered optical energy can, for example, disrupt pigmented chromophores and/or targets in a treatment region of the dermal layer of the skin, without affecting the surrounding regions (e.g., overlying epidermal layer, other portions of the dermal layer, and the like) or within other pigmented target areas of the skin or tissue surrounded by unaffected and non-targeted areas. In other implementations, the delivered optical energy can cause tattoo removal or alteration, or hemoglobin-related treatment.

In general, systems and corresponding methods are provided for treatment of pigmentary conditions in tissues. As discussed in greater detail below, the disclosed systems and methods employ electromagnetic radiation (EMR), such as laser beams, to deliver predetermined amounts of energy to a target tissue. The EMR can be focused to a focal region and the focal region can be translated or rotated in any direction with respect to the target tissue. The predetermined amount of radiation can be configured to thermally disrupt or otherwise damage portions of the tissue exhibiting the pigmentary condition. In this manner, the predetermined amount of energy can be delivered to any position within the target tissue for treatment of the pigmentary condition such as to improve the appearance thereof.

FIG. 1 illustrates one exemplary embodiment of a treatment system 10. As shown, the treatment system 10 includes a mounting platform 12, and emitter 14, and a controller 16. The mounting platform 12 can include one or more manipulators or arms 20. The arms 20 can be coupled to the emitter 14 for performing various treatments on a target tissue 22 of a subject 24. Operation of the mounting platform 12 and emitter 14 can be directed by a user, manually or using the controller 16 (e.g., via a user interface). In certain embodiments (not shown), the emitter can have a hand-held form factor and the mounting platform 12 can be omitted. In other embodiments, the mounting platform can be a robotic platform and the arms can be communicatively coupled to the controller for manipulation of the emitter.

The emitter 14 and controller 16 (and optionally the mounting platform 12) can be in communication with one another via a communications link 26, which can be any suitable type of wired and/or wireless communications link carrying any suitable type of signal (e.g., electrical, optical, infrared, etc.) according to any suitable communications protocol.

Embodiments of the controller 16 can be configured to control operation of the emitter 14. In one aspect, the controller 16 can control movement of EMR 30. As discussed in detail below, the emitter 14 can include a source 32 for emission of the EMR 30 and a scanning system 34 for manipulation of the EMR 30. As an example, the scanning system 34 can be configured to focus EMR 30 to a focal region and translate and/or rotate this focal region in space. The controller 16 can send signals to the source 32, via the communications link 26 to command the source 32 to emit the EMR 30 having one or more selected properties, such as wavelength, power, repetition rate, pulse duration, pulse energy, focusing properties (e.g., focal volume, Raleigh length, etc.). In another aspect, the controller 16 can send signals to the scanning system 34, via the communications link 26 to command the scanning system 34 to move the focal region of the EMR 30 with respect the target tissue 22 in one or more translation and/or rotation operations.

Embodiments of the treatment system 10 and methods are discussed herein in the context of targets within skin tissue, such as a dermal layer. However, the disclosed embodiments can be employed for treatment of any tissue in any location of a subject, without limit. Examples of non-skin tissues can include, but are not limited to, surface and sub-surface regions of mucosal tissues, genital tissues, internal organ tissues, and gastrointestinal tract tissues.

Figure 2:
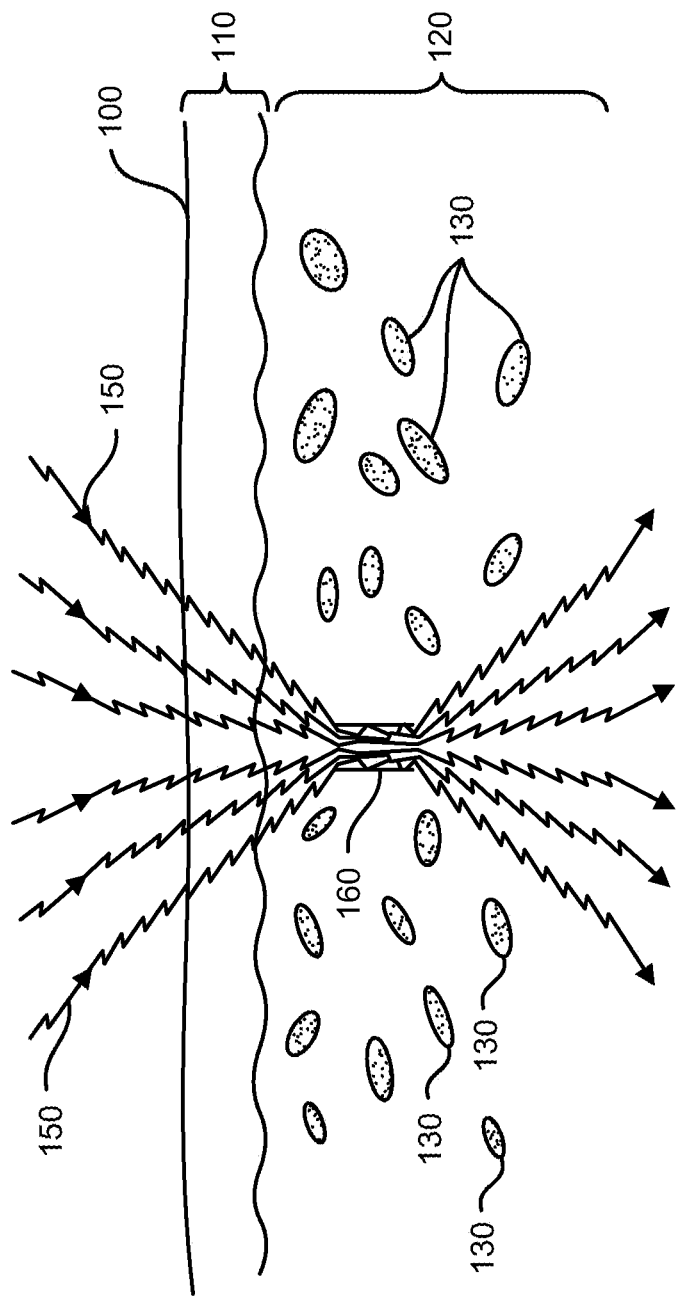
FIG. 2 is a schematic view of an illustration of a laser beam focused into a pigmented region of a dermal layer in a skin tissue.

FIG. 2 is a schematic view of an illustration of a laser beam focused into a pigmented region of a dermal layer in a skin tissue. The skin tissue includes a skin surface 100 and an upper epidermal layer 110 (or epidermis), which can be, e.g., about 30-120 µm thick in the facial region. The dermis can be slightly thicker in other parts of the body. For example, in general the thickness of the epidermis can range from about 30 µm (e.g., on the eyelids) to about 1500 µm (e.g., on the palm of the hand or soles of the feet). Such epidermis may be thinner or thicker than the examples above in certain conditions of the skin, for example psoriasis. The underlying dermal layer 120 (or dermis) extends from below the epidermis 110 to the deeper subcutaneous fat layer (not shown). Skin exhibiting deep or dermal melasma can include a population of pigmented cells or regions 130 that contain excessive amounts of melanin. Electromagnetic radiation (EMR) 150 (e.g., a laser beam) can be focused into one or more focal regions 160 that can be located within the dermis 120, or the epidermis, 110. The EMR 150 can be provided at one or more appropriate wavelengths that can be absorbed by melanin. EMR wavelength(s) can be selected based on one or more criteria described below.

FIG. 3 is a schematic illustration of a skin treatment system 300. The skin treatment system 300 includes a laser source 302 (e.g., a Q-switched laser) that can generate a laser beam 312. The laser beam can be received by an optical system 304 that can manipulate the laser beam 312 and direct a manipulated laser beam 314 to a focal region 316 in a tissue 306. Manipulation by the optical system 304 can involve one or more of changing the profile (e.g., intensity profile) of laser beam 312, changing the direction of propagation of laser beam 312, generating multiple laser beams from the laser beam 312 (e.g., by beam splitting using diffraction optics), and the like. The one or more laser beams (e.g., beam 314) emanating from the optical system 304 can be focused to one or more focal regions (e.g., focal region 316) in the tissue 306.

FIG. 4A is a schematic illustration of a diffractive optical setup 400. The diffractive optical setup includes a diffractive beam splitter 402 that receives an input laser beam 404 (e.g., from a Q-switched laser) and generates multiple output laser beams 406, 408 and 410 (also referred to as "active orders"). Diffracted laser beams 406, 408 and 410 can be assigned diffraction orders based on their direction of propagation. For example, laser beam 406 can have a diffraction order of "0," laser beam 408 can have a diffraction order of "1," and laser beam 410 can have a diffraction order of "-1." The angle between the outermost diffraction orders (e.g., $\alpha_f$) can be referred to as the full angle, and the angle between the adjacent diffraction orders (e.g., $\alpha_s$) can be referred to as the separation angle.

A diffraction beam splitter that can receive a single laser beam and output "m" beams having their respective direction of propagation rotated around a given axis can be referred to as a 1×m beam splitter. For example, diffractive beam splitter 402 that receives a laser beam 404 and outputs three laser beams 406, 408 and 410 having their respective direction of propagation rotated around the y-axis can be referred to as 1×3 beam splitter. In some implementations, a beam splitter can generate an array of output beam with cross-sections arranged along two dimensions ("two-dimensional beam matrix"). FIG. 4B illustrates an exemplary two-dimensional beam matrix generated by two-dimensional diffraction of a laser beam by a diffractive beam splitter.

Figure 5:
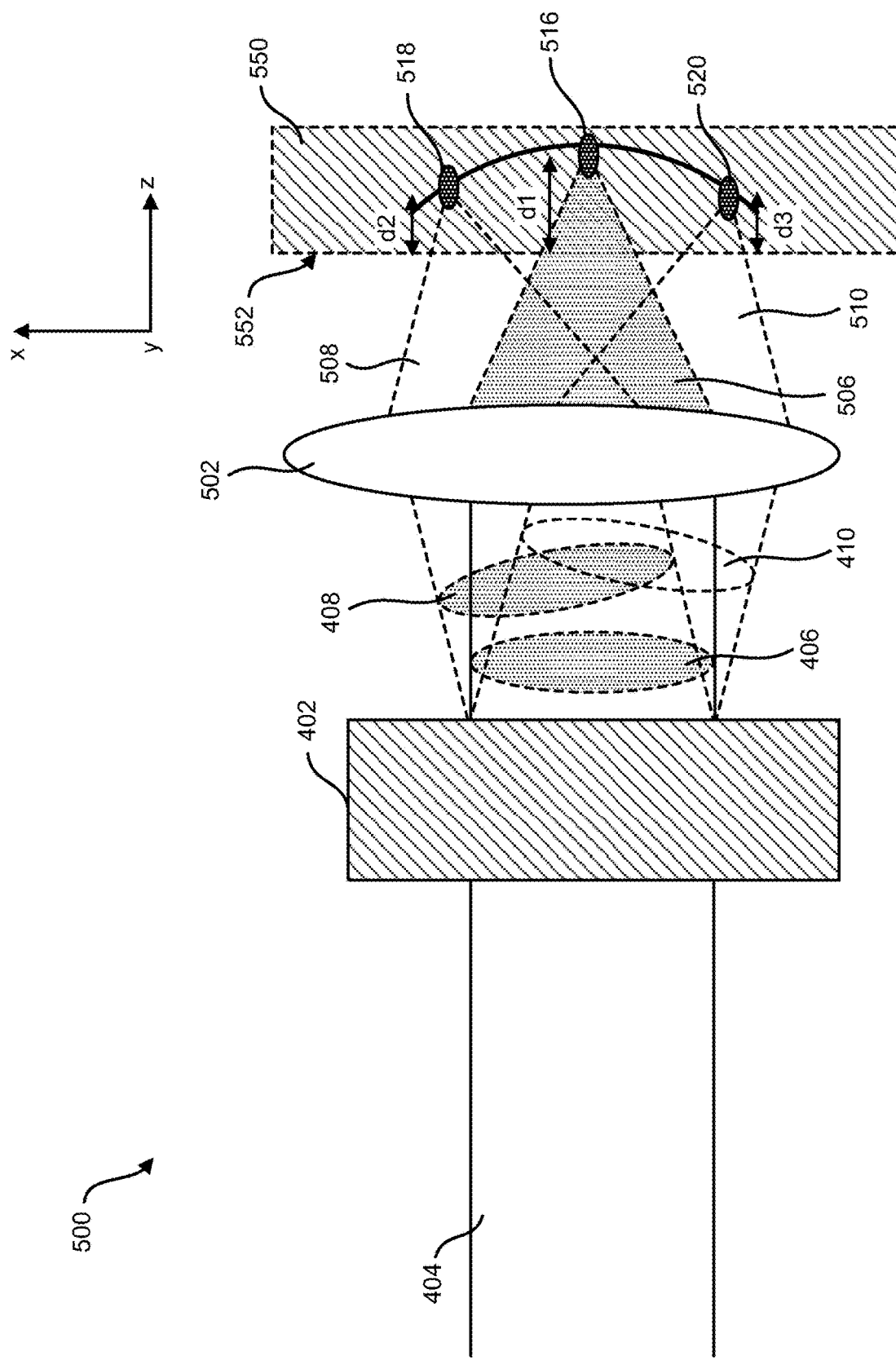
FIG. 5 is a schematic illustration of an exemplary embodiment of an optical system for generating multiple focal volumes from a single laser beam.

FIG. 5 illustrates an exemplary optical system 500 for generating multiple focal volumes from a single laser beam. The optical system 500 includes the diffractive beam splitter 402 and a lens 502 optically down-beam from the diffractive beam splitter 402. As described above, the diffractive beam splitter 402 can generate multiple output laser beams 406, 408 and 410 that impinge on the lens 502. The lens 502 can produce converging beams 506, 508 and 510 from the output laser beams 406, 408 and 410, respectively. The converging beams 506, 508 and 510 can focus to focal volumes 516, 518 and 520, respectively in the tissue 550. The tissue can be arranged, for example, along the x-axis. This can result in the focal volumes 516, 518 and 520, located at different depths with respect to the tissue surface 552 facing the optical system 500. For example, the focal volumes 516, 518 and 520 can be located at a depths $d_1$, $d_2$, and $d_3$, respectively. According to some embodiments, the different depths $d_1$, $d_2$, and $d_3$ are a result of a field curvature of the optical system 500. The focal volumes 516, 518 and 520 can be arranged along a curved line 530. The curvature of the curved line 530, can depend on the separation angle between output laser beams 406, 408 and 410 and/or focal length of the lens 502.

Figure 6:
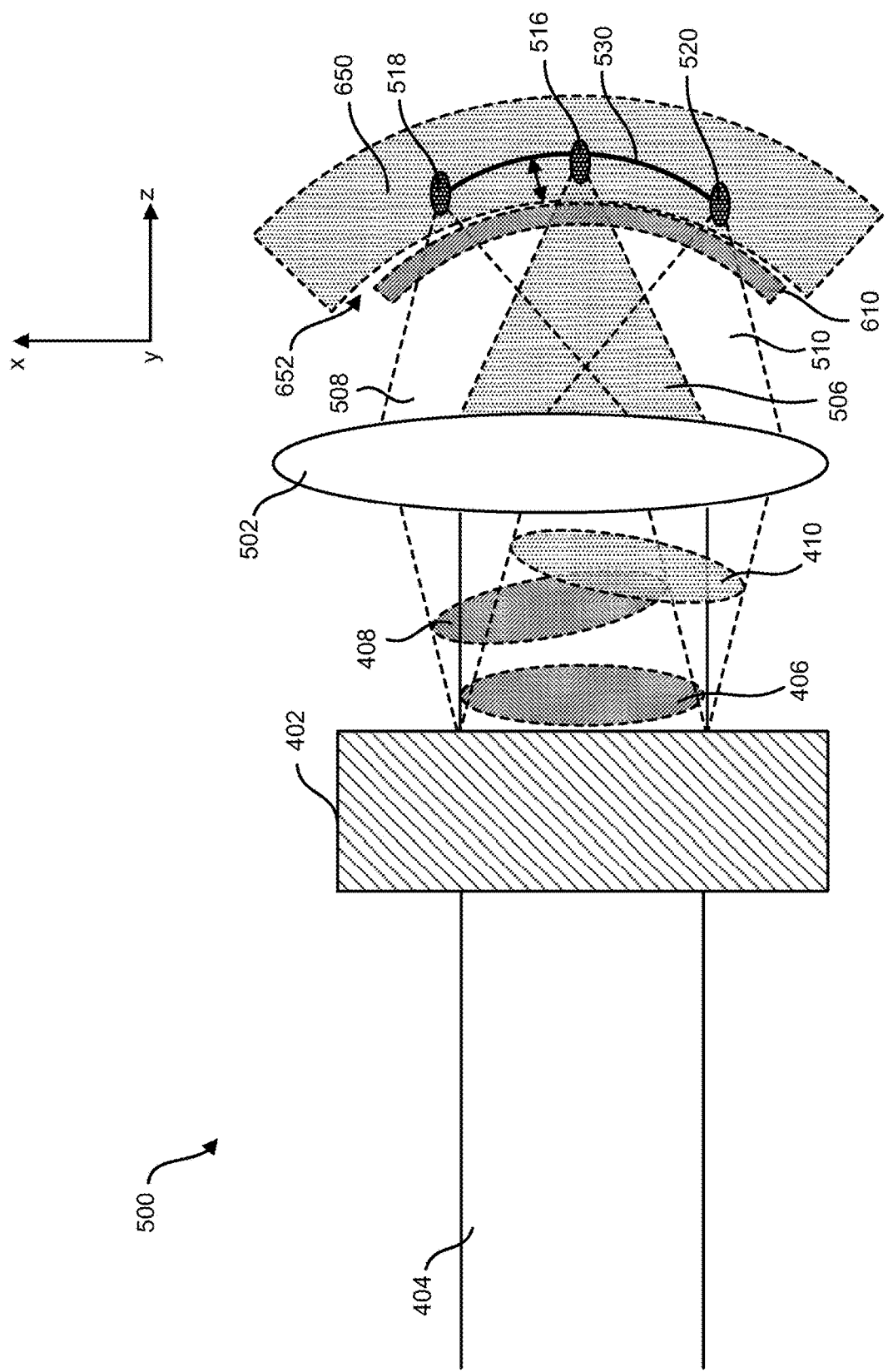
FIG. 6 illustrates the optical system of FIG. 5 including a contacting surface.

FIG. 6 illustrates the optical system 500 having a contacting surface 610. The contacting surface 610 can serve as an interface between the optical system 500 and tissue 650 having a tissue surface 652. The contacting surface 610 can alter the geometry of the tissue surface 652. For example, the contacting surface 610 having a given curvature can alter the shape of the tissue surface 652 (e.g., to conform to the curvature of the contacting surface 610). The curvature of the contacting surface 610 can be determined based on the curvature of the curved line 530 along which the focal volumes 516, 518 and 520 are arranged. This can allow for the focal volumes 516, 518 and 520 to be located at similar depths from the tissue surface 652. Uniformity in the depth of the focal volumes 516, 518 and 520 can allow for treatment of a given tissue layer in the tissue 650 (e.g., dermal layer in skin) without affecting other tissue layers.

Figure 7:
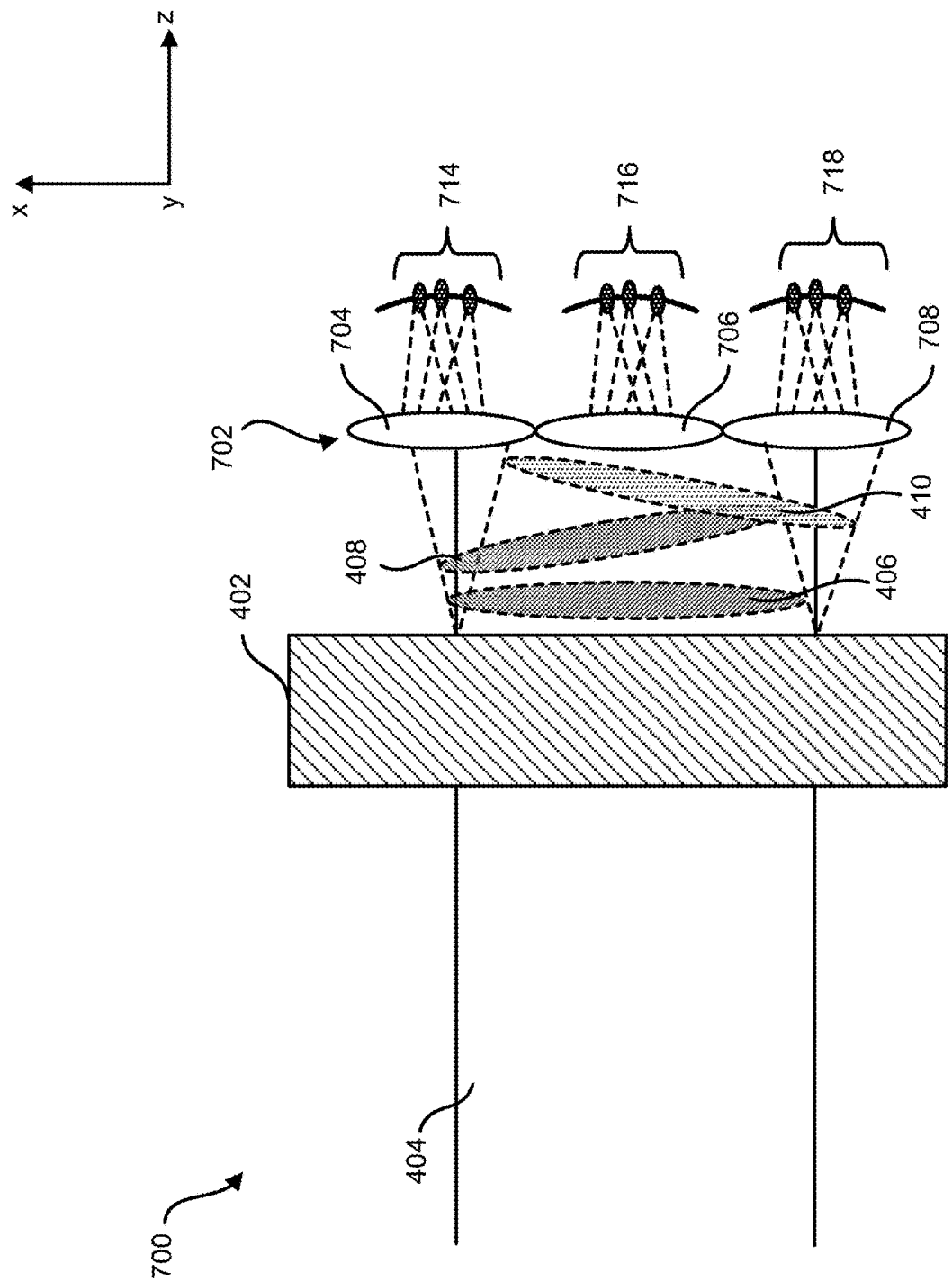
FIG. 7 is a schematic illustration of an exemplary optical system for generating multiple arrays of focal volumes from a single laser beam.

FIG. 7 illustrates an exemplary optical system 700 for generating multiple focal volumes from a single laser beam. The optical system 700 includes the diffractive beam splitter 402 and a lens array 702 optically down-beam from the diffractive beam splitter 402. As described above, the diffractive beam splitter 402 can generate multiple output laser beams 406, 408 and 410 that impinge on the lens array 702. The lens array 702 can include lenses 704, 706, and 708. One or more of these lenses 704, 706, and 708 can receive one or more of the output laser beams 406, 408 and 410. As a result, a lens in the lens array 702 can generate multiple converging beams that converge to multiple focal volumes. For example, lens 704 can generate an array of focal volumes 714, lens 706 can generate an array of focal volumes 716, and lens 708 can generate an array of focal volumes 718. Each array of focal volumes can be arranged along a curved line having a curvature. In some implementations, the curvature of the array of focal volumes (e.g., 714, 716, 718, etc.) can be less than that of the curvature of focal volumes obtained by a single lens (e.g., focal volumes 516, 518 and 520 from lens 502). This can be desirable because a lower curvature of focal volumes can allow the focal volumes to remain at similar depths in a tissue (e.g., in the same tissue layer).

Figure 8:
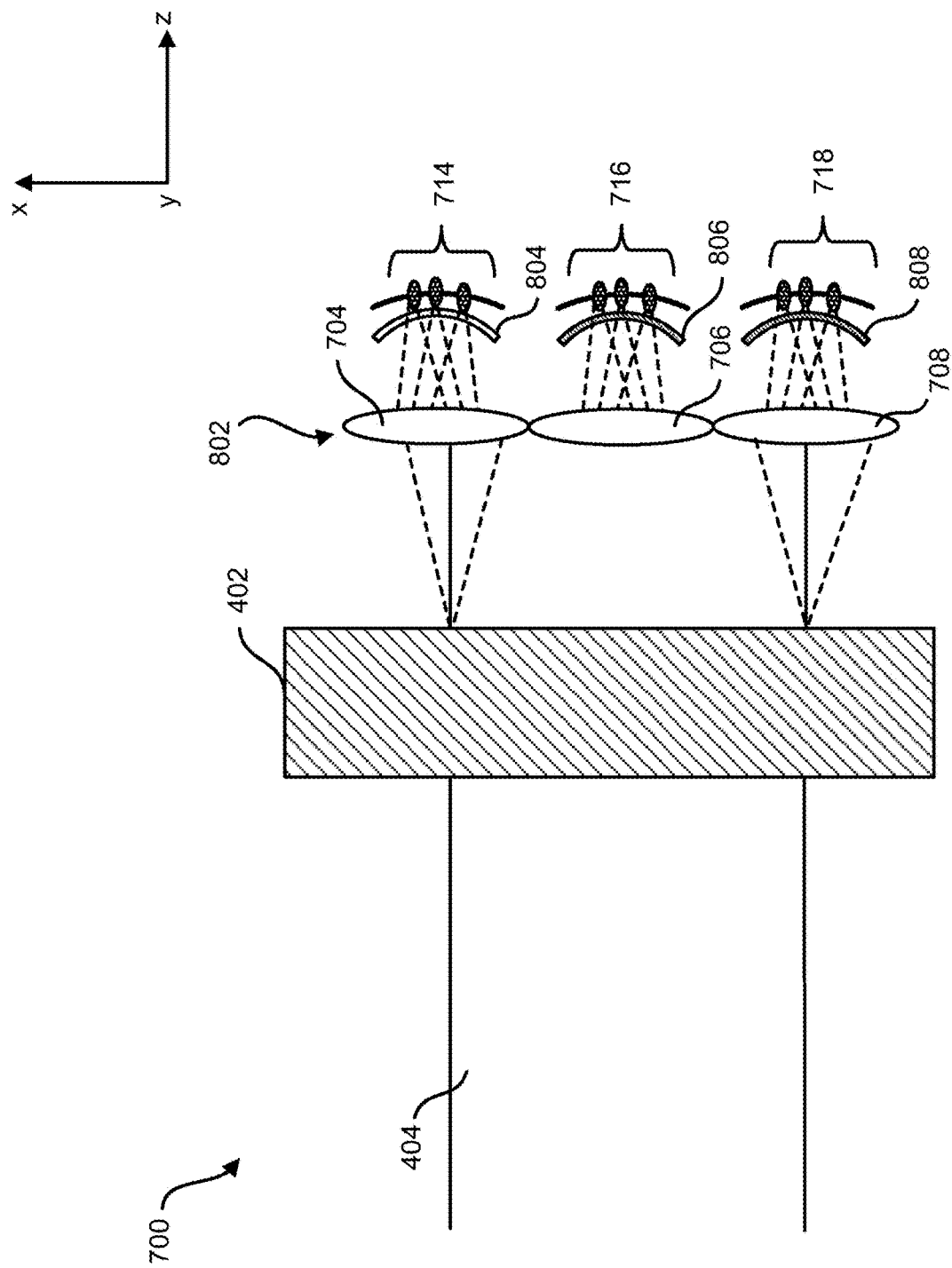
FIG. 8 illustrates the optical system of FIG. 7 including a contacting surface.

FIG. 8 illustrates the optical system 700 having an array of contacting surfaces 802. The array of contacting surfaces can include multiple contacting surfaces 804, 806 and 808. The contacting surfaces 804, 806 and 808 can alter the geometry of a tissue surface (e.g., to conform to the curvature of the contacting surface 610). The curvature of the contacting surfaces 804, 806 and 808 can be determined based on the curvature of the array of focal volumes 714, 716, 718, respectively.

Figure 9:
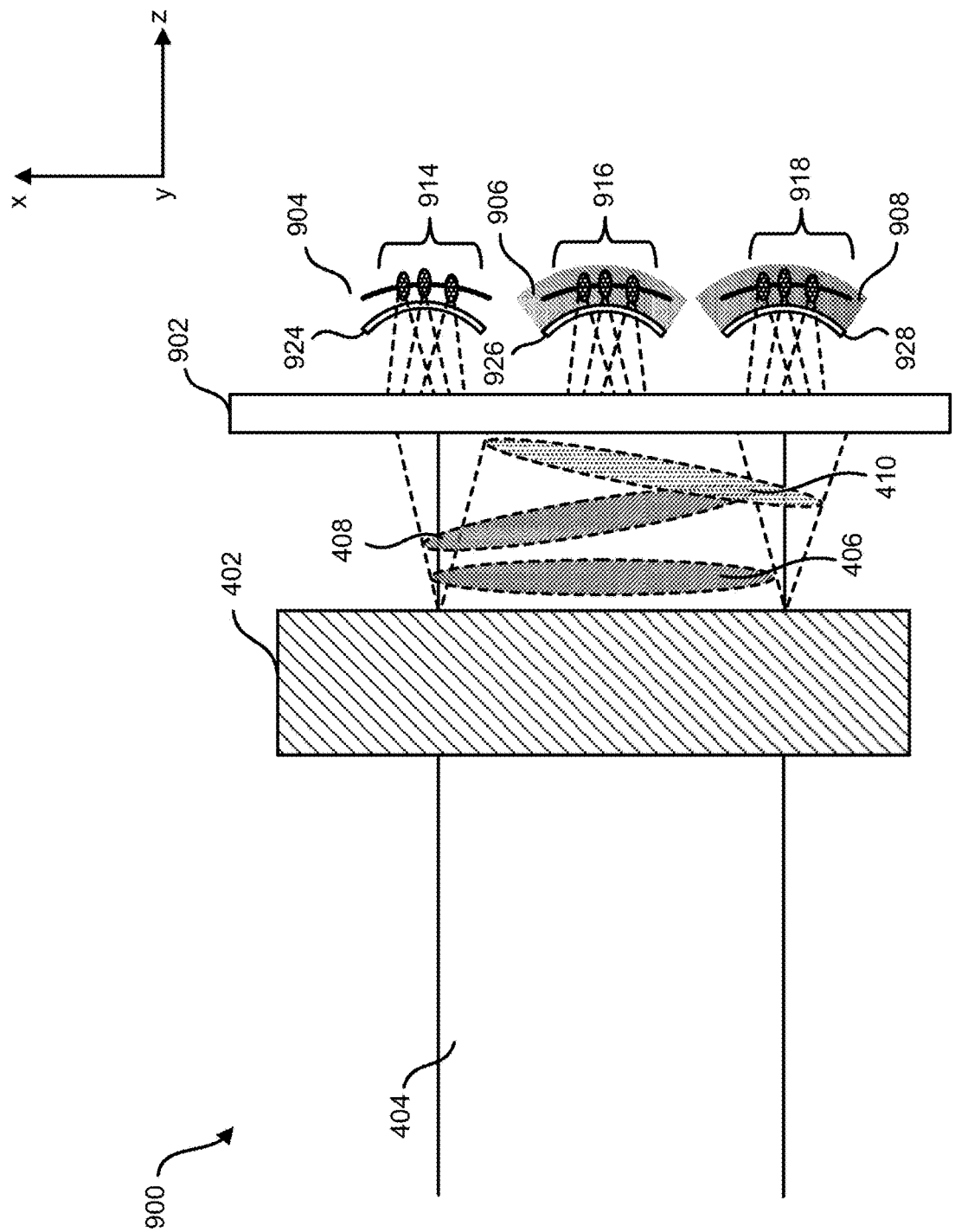
FIG. 9 is a schematic illustration of an exemplary optical system for generating multiple arrays of focal volumes from a single laser beam using a diffractive plate.

FIG. 9 illustrates an exemplary optical system 900 for generating multiple arrays of focal volumes from a single laser beam. The optical system 900 include the diffractive beam splitter 402 and a diffractive plate 902 (e.g., array of Fresnel zone plates) optically down-beam from the diffractive beam splitter 402. As described above, the diffractive beam splitter 402 can generate multiple output laser beams 406, 408 and 410 that impinge on the diffractive plate 902. The diffractive plate 902 can produce multiple arrays of focal volumes 914, 916 and 918 in the tissue regions 904, 906 and 908. For example, an array of Fresnel zone plate can include multiple Fresnel zone plates (not shown) and each Fresnel zone plate can generate an array of focal volumes from the output laser beams 406, 408 and 410 (e.g., a first Fresnel zone plate can generate focal volumes 914, a second Fresnel zone plate can generate focal volumes 916, a third Fresnel zone plate can generate focal volumes 918, etc.). The optical system can also include contacting surfaces 924, 926 and 928 that can alter the geometry of the tissue regions. This can allow, for example, arrays of focal volumes to remain at similar depths in tissue regions (e.g., array of focal volumes 914, 916 and 918 in tissue regions 904, 906 and 908, respectively).

Figure 10A:
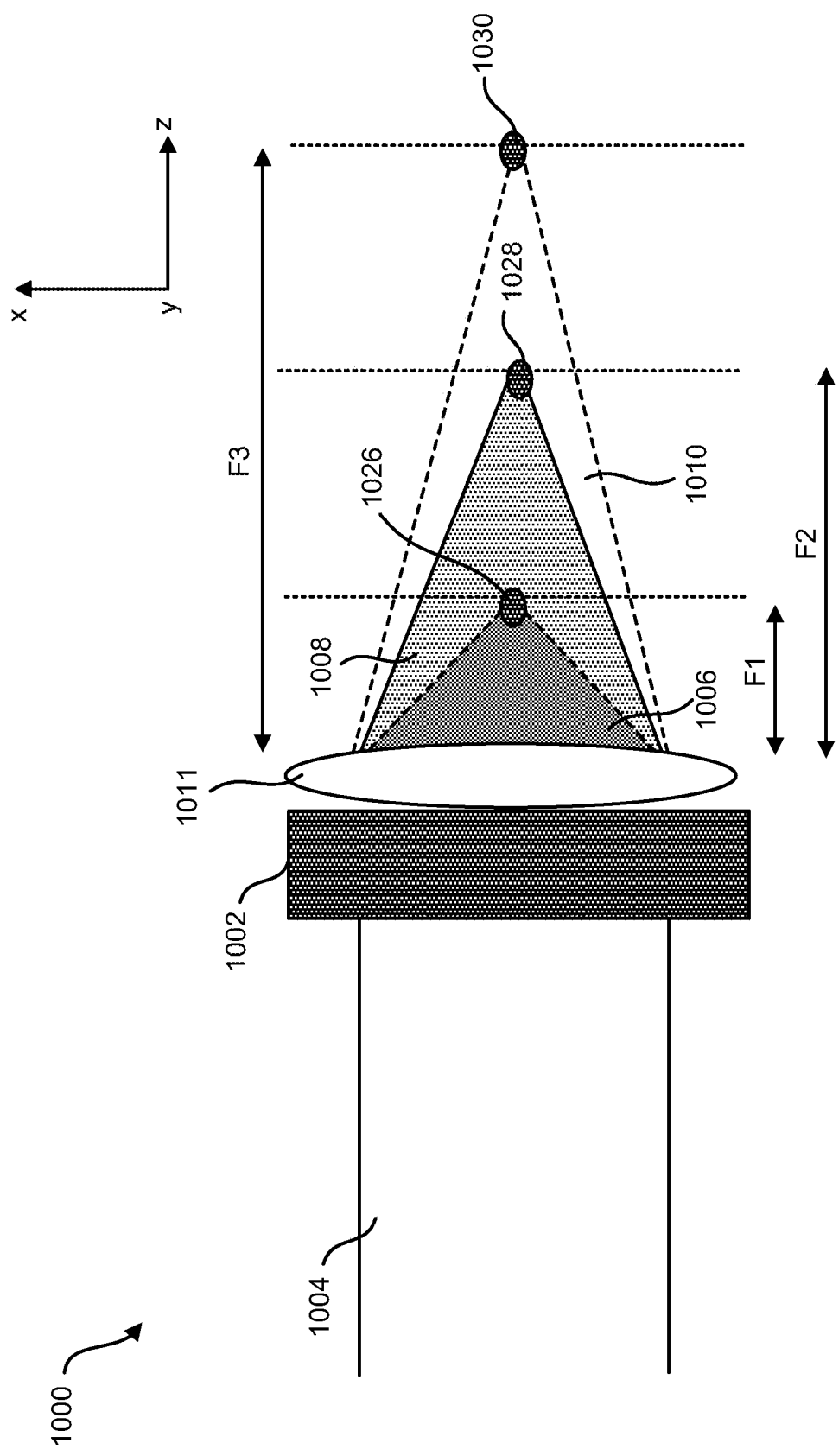
FIG. 10A is a schematic illustration of an exemplary embodiment of a diffractive optical setup that generates multiple focal regions at multiple depths in the target tissue.

FIG. 10A is a schematic illustration of an exemplary embodiment of a diffractive optical setup 1000 that generates multiple focal regions at multiple depths in the target tissue. The diffractive optical element includes a diffractive element 1002 (e.g. Part No. MF-001-I-Y-A from Holo/OR of Tel Aviv, Israel), that can receive an input laser beam 1004 (e.g., from a Q-switched laser) and generate multiple output laser beams 1006, 1008, and 1010 having different divergences, such that they focus at various distances when focused by an optical element 1011 (e.g., a lens, a Fresnel zone plate, etc.). For example output laser beams 1006, 1008, and 1010 can be focused at focal regions 1026, 1028 and 1030, respectively (that are located at distances $F_1$, $F_2$ and $F_3$, respectively, from the optical element 1011). According to some embodiments, the optical element 1011 can include, for example, a refractive optical element (e.g., a lens, multi-lens array, etc.) and a diffractive optical element (e.g. a Fresnel zone plate, array of Fresnel zone plates, etc.). Additionally, according to some embodiments, the diffractive element 1002 can distribute the input laser beam 1004 in various proportions (e.g., based on intensity) among the output laser beams 1006, 1008, 1010. For example, the output laser beam 1010 focused farthest from the optical element 1011 can include about half of the energy of the input laser beam 1004, and the other two output laser beams 1006 and 1008 each can include about a quarter of the energy of the input laser beam 1004 each.

Figure 10B:
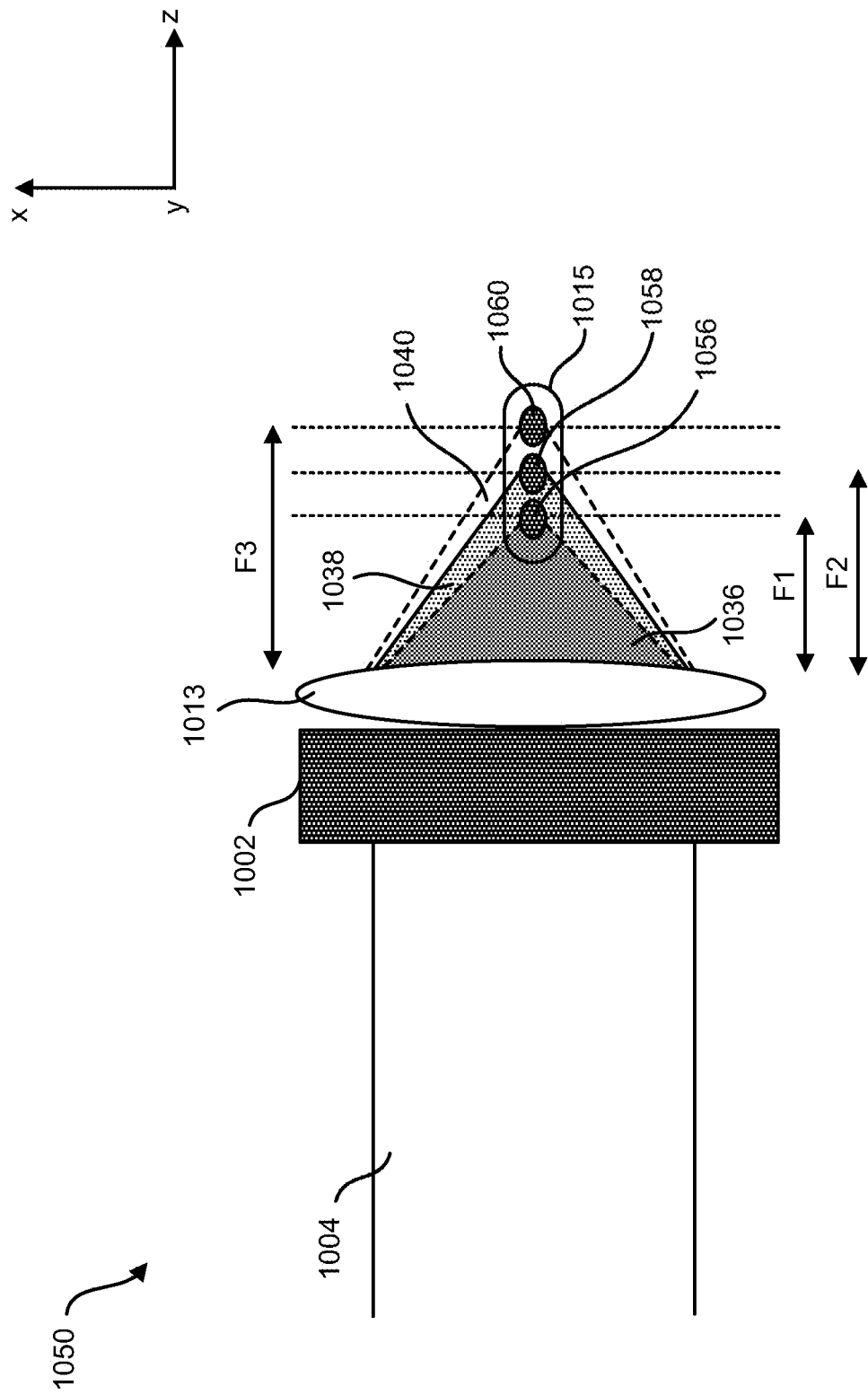
FIG. 10B is a schematic illustration of an exemplary embodiment of a diffractive optical setup that generates multiple focal regions that form a treatment volume extending along the depth of the target tissue.

FIG. 10B is a schematic illustration of an exemplary embodiment of a diffractive optical setup 1050 that generates multiple focal regions that form a treatment volume extending along the depth of the target tissue. The optical set up 1050 can include a diffractive element 1002 that can receive an input laser beam 1004 (e.g., from a Q-switched laser) and generate multiple output laser beams 1036, 1038, and 1040 focused at focal regions 1056, 1058 and 1060, respectively, by an optical element 1013 (e.g., a lens, multi-lens array, a Fresnel zone plate, array of Fresnel zone plates, etc.). The focal regions 1056, 1058 and 1060 can form a treatment volume 1015. The treatment volume can be elongated along the depth (z-direction), the focal regions 1056, 1058 and 1060 can be arranged along the depth of the target tissue. For example, the focal regions can overlap each other, can be in close proximity to each other (e.g., separated by a distance less than two times a Rayleigh length of a single focal region of a laser beam having a characteristic frequency [e.g., central frequency] of the laser beam 1004), and the like. According to some versions the Rayleigh length is given by:

$$z_R = \frac{\pi * \omega_0^2}{\lambda}$$

where, $z_R$ is the Rayleigh length, $\omega_o$ is a radius of the beam at focus, and $\lambda$ is wavelength of the beam. In some embodiments, numerical aperture (NA) controls the radius of the beam at focus ($\omega_o$) and it is appropriate to approximate this relationship with:

$$NA \cong \frac{\lambda}{\pi \omega_o}$$

The treatment volume can extend from a first depth (e.g., 0.2 mm) to a second depth (e.g., 0.7 mm). In some implementations, portion of the target tissue located in the treatment volume can be heated by the one or more focal regions in the treatment volume. In other implementations, plasma can be generated in one or more portions of the treatment volume (e.g., by laser induced optical breakdown (LIOB), by laser induced thermal breakdown (LITB), etc.). In some implementations, plasma can be generated in and around a target (e.g., chromophore, tattoo ink, etc.) in the treatment volume.

Figure 11:
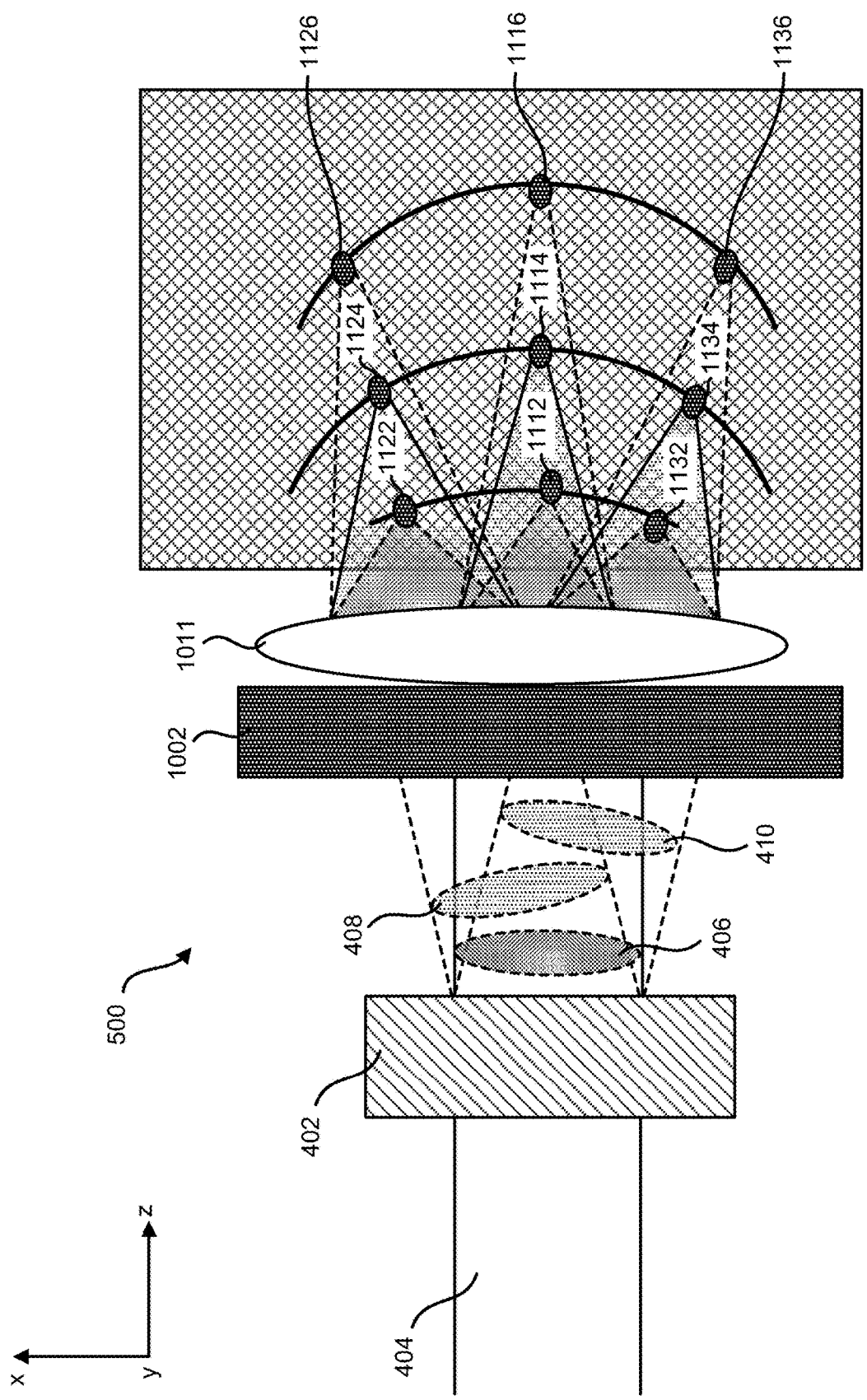
FIG. 11 is a schematic illustration of the exemplary optical system in FIG. 4A including a diffractive element and an objective to generate an array of focal volumes.

FIG. 11 is a schematic illustration of the optical system 500 including the diffractive element 1002 an optical element 1011 (e.g., a lens, multi-lens array, a Fresnel zone plate, array of Fresnel zone plates, etc.). The diffractive element 1002 can be located optically down-beam from the diffractive beam splitter 402. The output laser beams 406, 408 and 410 from the diffractive beam splitter 402 can impinge on the diffractive element 1002. The diffractive element 1002 can be configured to produce multiple beams that can be focused at different focal lengths (e.g., at the various focal lengths $F_1$, $F_2$ and $F_3$) by the optical element 1011 for each output beam 406, 408, and 410. This can result in an array of focal volumes distributed at different depths from the tissue surface and along the x-axis. For example, the diffractive element 1002 can receive the output beam 406 and generate focal volumes 1112, 1114, and 1116 that can correspond to focal lengths $F_1$, $F_2$, and $F_3$ when focused by an optical element 1011. The diffractive element 1002 can receive the output laser beam 408 and generate focal volumes 1122, 1124, and 1126 that can correspond to focal lengths $F_1$, $F_2$, and $F_3$ when focused by the optical element 1011. The diffractive element 1002 can also receive the output laser beam 410 and generate focal volumes 1132, 1134 and 1136 that can correspond to focal lengths $F_1$, $F_2$, and $F_3$ when focused by the optical element 1011. Additionally, the focal volumes for a given focal length can be arranged along a curve line that has a curvature that depends on the separation angle between output beams and/or focal length of the diffractive element 1002.

Figure 12:
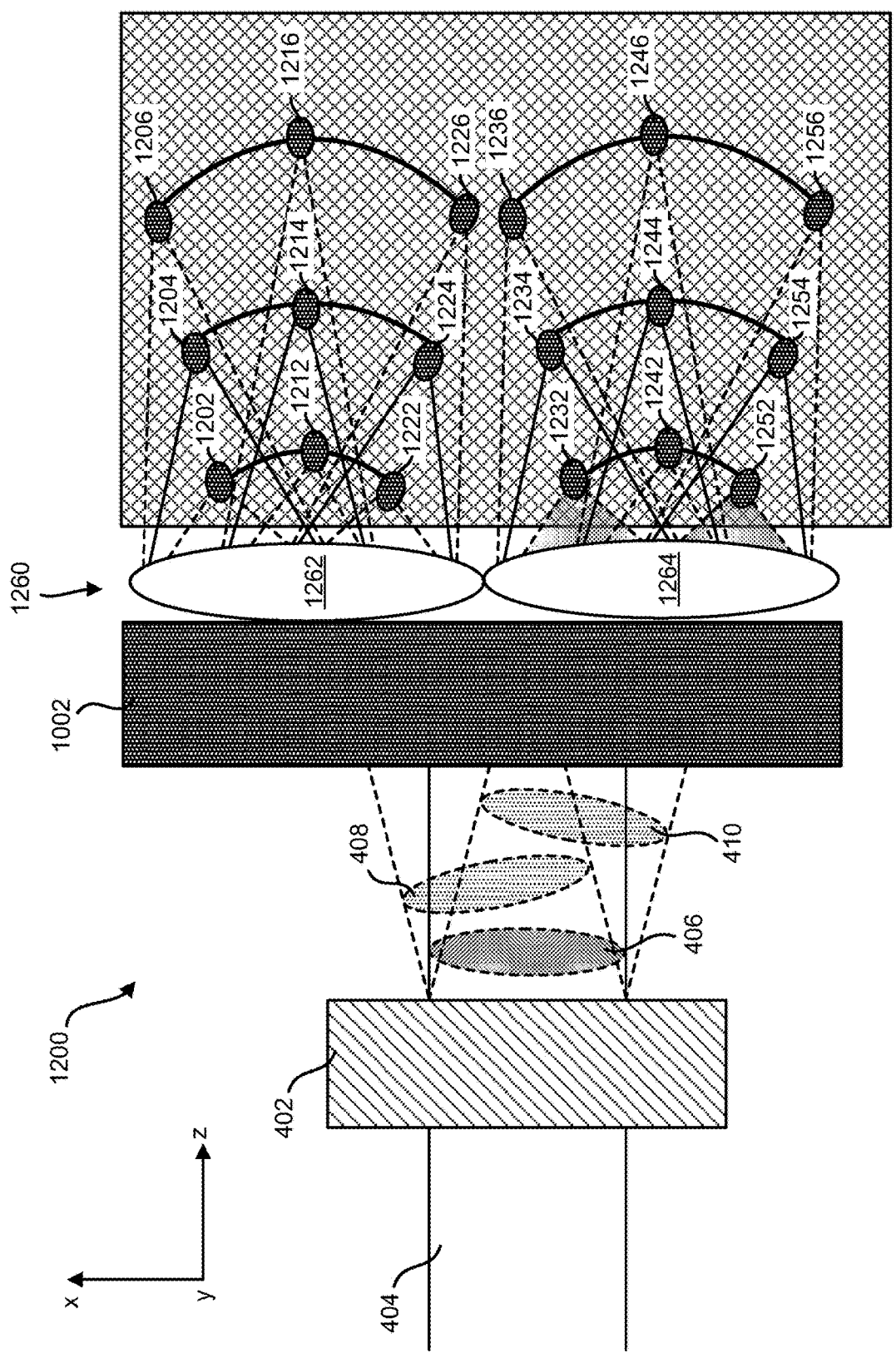
FIG. 12 is a schematic illustration of the exemplary optical system in FIG. 4A including a diffractive optical element and multi-lens array to generate multiple arrays of focal volume.

In some implementations, the diffractive beam splitter 402 can produce a two-dimensional array of beams (e.g. two-dimensional beam matrix in the x-y plane). If a two-dimensional beam matrix impinges on the diffractive element 1002, the diffractive element 1002 can generate a three-dimensional array of focal volumes in the tissue. This can allow for simultaneous treatment of three-dimensional region by a single laser beam 404. FIG. 12 is a schematic illustration of the exemplary optical system 1200 including the diffractive optical element 1002 and multi-lens array 1260 to generate multiple arrays of focal regions. The multi-lens array 1260 includes a first lens 1262 and a second lens 1264. The diffractive optical element 1002 can generate multiple beams that can be focused by the lenses of the multi-lens array into an array of focal regions. For example, the multiple beams generated by the diffractive optical element 1002 (from output laser beams 406, 408, 410, etc.) can be focused to a first array of focal volumes 1202-1206, 1212-1216 and 1222-1226 by the first lens 1262. The multiple beams generated by the diffractive optical element 1002 (from output laser beams 406, 408, 410, etc.) can be focused to a second array of focal volumes 1232-1236, 1242-1246 and 1252-1256 by the second lens 1264. In some implementations, the multi-lens array 1260 can include a two-dimensional array of lenses (e.g., in the x-y plane) where one or more lenses in the two-dimensional array can generate an array of focal regions (e.g., arranged in three dimensions). In some implementations, the multi-lens array 1260 can be an array of Fresnel zone plates where first lens 1262 and second lens 1264 represent Fresnel zone plates. In some implementations, the optical system in FIG. 11 and FIG. 12 can act as optical demultiplexer where multiple focal regions can be generated by a single input optical beam (e.g., laser beam 404).

Figure 13:
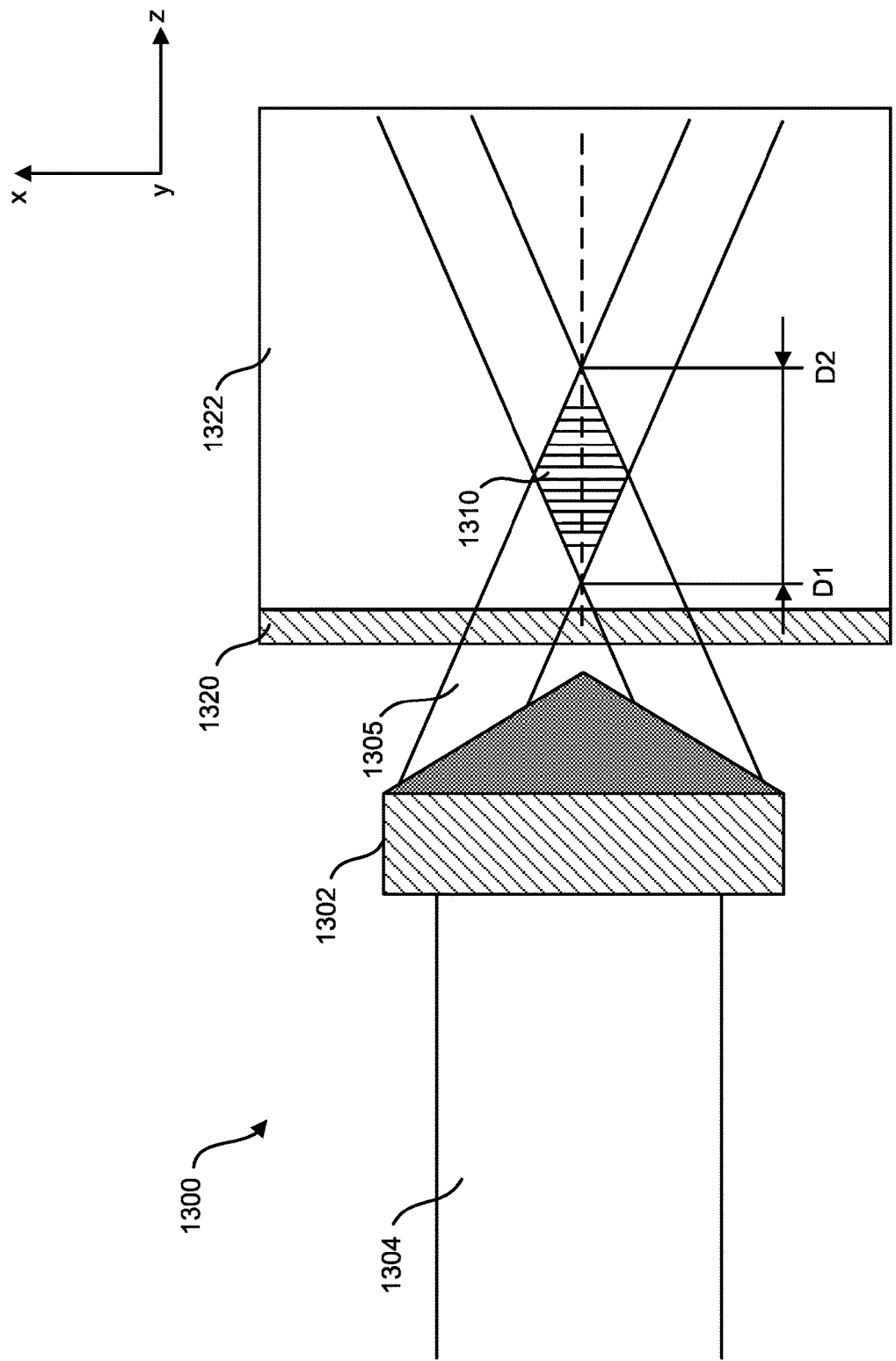
FIG. 13 is a schematic illustration of an optical system configured to generate a quasi-diffraction-free beam having a focal region in a target tissue.

FIG. 13 is a schematic illustration of an optical system 1300 configured to generate a quasi-diffraction-free beam having a focal region in a target tissue. The optical system 1300 includes an optical element 1302 (e.g., axicon) that can receive an input laser beam 1304 and generate a quasi-diffraction free beam (QDFM) 1305. The QDFM 1305 can have a focal region 1310 that can extend from a first depth D1 in the target tissue to a second depth D2 in the target tissue. The optical element 1302 can have a large numerical aperture (e.g., greater than 0.3, between 0.3 and 1, between 0.4 and 0.8, and between 0.4 and 0.6). This can prevent undesirable interaction (e.g., generation of plasma, heating, etc.) between upper layers of the target tissue (e.g., epidermis for a skin tissue) and QDFM 1305. In some implementations, the extent of the focal region 1310 along the depth of the target tissue (e.g., along z-direction) can be longer than the extent of the focal region of a beam which suffers larger diffraction (e.g., Gaussian beam). As a result, for a given numerical aperture, a QDFM can allow for treatment along larger depths in the target tissue. This can obviate the need for scanning of the focal region along the depth (e.g., z-axis).

The aforementioned optical systems (e.g., optical system 1050, 1300, etc.) can allow for microfractional treatment (e.g., selective treatment of desired regions of the target tissue. For example, it can be desirable to treat an underlying layer of the target tissue (e.g., dermal layer of a skin tissue) without undesirable effects by the treatment beam on the overlying layer of the target tissue (e.g., epidermal layer of the skin tissue). In another example, patients with darker skin type can have a higher density of melanin that can lead to undesirable absorption of the treatment beam. This can cause unwanted hyper/hypo-pigmentation and inflammation. Therefore, it can be desirable to reduce interaction between the treatment beam and the target tissue.

Microfractional treatment can be achieved by designing the optical system to have a high numerical aperture (e.g., greater than 0.3). Having a high numerical aperture can reduce the energy density of the incoming treatment beam in the epidermal layer and can focus the treatment beam to a small focal region in the dermal layer. For example, a numerical aperture of 0.5 for a treatment beam centered at about 1064 nm in air can generate a beam waist (cross section of the focal region) of about 4 micrometers. Due to small beam waist (e.g., close to the size of a cell in the target tissue), the recovery time after treatment can be small.

However, due to the small focal region of the treatment beam, treatment time can be long which can be undesirable. Hence, it is desirable to treat a larger volume of the target tissue while keeping the numerical aperture large (greater than 0.3). This can be done by increasing the volume of the target tissue ("treatment volume") that can be treated (e.g., simultaneously) by irradiating one or more treatment beams on the target tissue. In some implementations, the target volume can include a single focal region of a treatment beam (e.g., focal region 1310 in FIG. 13). In other implementations, the target volume can include an array of focal volumes distributed in three dimensions (e.g., as illustrated in FIG. 11), or multiple arrays of focal volumes distributed in three dimensions (e.g., as illustrated in FIG. 12) that are generated from a single input beam (e.g., laser beam 404 from a Q-switch laser). In yet other implementations, the treatment volume can include multiple focal volumes arranged along the depth (e.g., z-axis) of the target tissue (e.g., FIGS. 10A and 10B). Having a treatment volume that extends along the depth of the target tissue can obviate the need for scanning the focal region along the depth (e.g., along the z-direction). Additionally or alternately, it can allow for treating regions of the target tissue that might otherwise be too deep for treatment. In some implementations, the wavelength of the treatment beam can be chosen such that the treatment beam can penetrate into the target tissue. This choice of the wavelength can be based on properties of the target tissue (e.g., scattering, absorption, etc.). In some implementations, the wavelength of the treatment beam can range from about 200 nm to about 2000 nm (e.g., 1064 nm).

Treatment in the treatment volume can be performed multiple ways. For example, treatment can be performed by generating a plasma in the treatment volume (ablative treatment). The generation of plasma can be selective within the treatment volume. For example, plasma can be generated in and around one or more targets (e.g., tattoo ink, chromophore, etc.) in the treatment volume. The generation of plasma can also be non-selective. For example, plasma can be generated in one or more regions of the treatment volume without a preference for a target in the treatment volume. In some implementations, treatment can be performed without the generation of a plasma. For example, treatment can be performed by heating up the target tissue in the treatment volume (non-ablative treatment). The type of treatment (ablative or non-ablative) can depend on the intensity of the treatment beam.

Figure 14B:
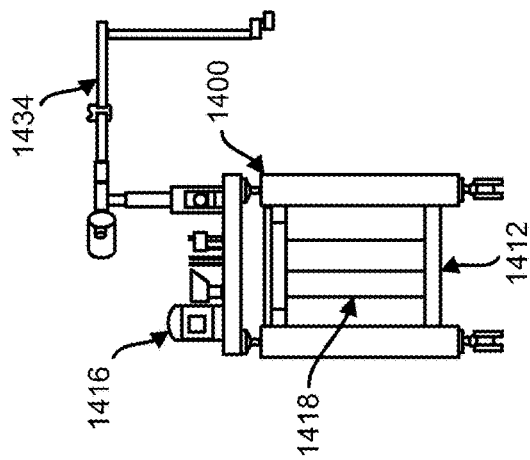
FIG. 14B is an illustration of a second side view of the exemplary optical system in FIG. 14A.
Figure 14C:
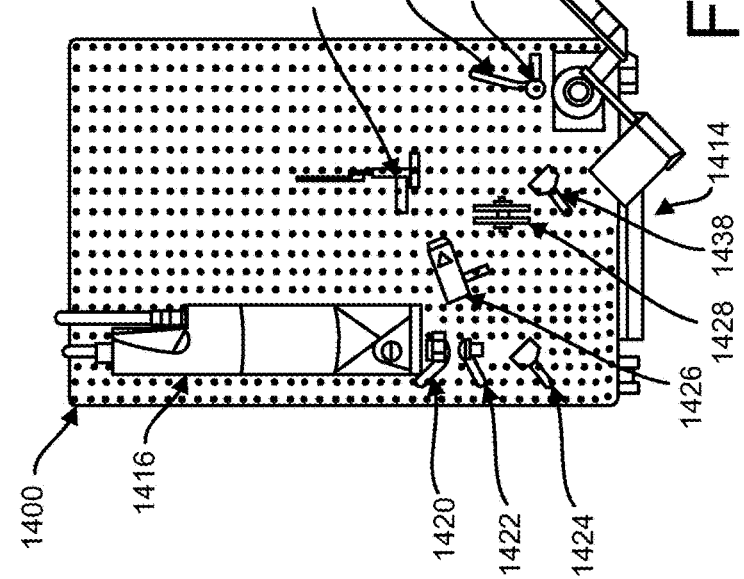
FIG. 14C is an illustration of a top view of the exemplary optical system in FIG. 14A.
Figure 14A:
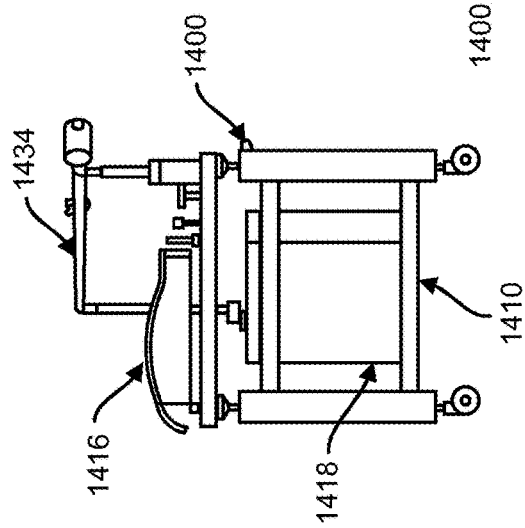
FIG. 14A is an illustration of a first side view of an exemplary optical system 1400 for multispot laser treatment.

FIGS. 14A-C are illustrations of an exemplary optical system 1400 for multispot laser treatment. The optical system 1400 is shown in a side view 1410 in FIG. 14A, a front view 1412 in FIG. 14B, and a top view 1414 in FIG. 14C. The optical system 1400 includes a Quantel Q-Smart 450 laser source 1416. The laser source 1416 generates laser pulses at a rate up to 10 Hz having a central wavelength of about 1064 nm, a pulse duration of 6 nanoseconds (nS), and an energy per pulse of about 450mJ. The laser source 1416 is supported by a console 1418. The console 1418 provides a chiller and a power supply to the laser source 1416. Additionally, the console 1418 provides interfaces for controlling and monitoring the laser source 1416.

Referring now to the top view 1414 in FIG. 14C of the optical system 1400, the laser source 1416 is configured to direct a laser beam out its exit aperture (not shown) and toward an optical assembly. According to some embodiments, the laser is first directed to a waveplate 1420 and then to a polarizer 1422. The polarizer 1422 can be configured to direct a first polarization of the laser beam to a first laser reflector 1424 and a second polarization of the laser beam to a beam dump 1426. By rotation of the waveplate 1420, the proportion of the laser beam being directed toward the first laser reflector 1424 can be varied. According to some embodiments, one or more neutral density (ND) filters shown here in a filter wheel assembly 1428 can be placed along a path of the laser beam reflected by the laser reflector 1424. The ND filters can be configured to filter a prescribed portion of the laser beam directed to it from the laser reflector 1424. The laser beam transmitted by the ND filter is reflected by a second laser reflector 1430. The reflected laser beam is incident on a beam combiner 1432. The beam combiner 1432 transmits the laser beam which is then directed into an articulating arm 1434. A visible aiming diode 1436 can produce a coherent visible beam of low power (e.g. 530 nm and 5 mW). The laser diode 1436 can direct the visible beam towards a first visible reflector 1438. The first visible reflector 1438 reflects the visible beam toward the beam combiner 1432, which reflects the visible beam toward the articulating arm 1434. The reflected visible beam from the beam combiner 1432 and the transmitted laser beam from the beam combiner 1432 can be combined (e.g., can spatially overlap) into a combined beam. The reflected visible beam and the transmitted laser beam can be controlled such that the two are collinear in the articulating arm 1434 (e.g., orientation of the laser reflectors 1424 and 1430 and laser diode 1436 can be controlled).

FIGS. 15A-C illustrates an exemplary test handpiece 1500. The handpiece 1500 is shown in a front view 1510 in FIG. 15A, a sectioned view 1520 in FIG. 15B, and a top view 1530 in FIG. 15C. As illustrated in the sectioned view 1520, the handpiece 1500 can couple to an end of the articulating arm 1434 at an arm adapter 1532. The combined beam can be directed out of the articulating arm 1434 along an optical axis 1534 in the handpiece 1500. The combined beam passes through a diffractive optical element (DOE) 1536. According to some embodiments, the DOE 1536 is a 9×9 2D beam splitter having a half degree separation angle (e.g. HOLO/OR Part No. MS-027-I-Y-A from HOLO/OR of Tel Aviv, Israel). The DOE 1536 generates a number of beamlets from the combined beam. The beamlets are focused by an objective 1538. For example, objective 1538 can be an Edmunds Optic Part No. 69-860 having an effective focal length of about 7.5 mm. The beamlets pass through an optical window 1540 (or "window"), and are focused at multiple focuses. An exemplary window 1540 can be an Edmunds Optics Part No. 48-919, which is a 1 mm thick sapphire window. The window 1540 is held in a frame 1542 which is static. The arm adapter 1532, DOE 1536, and objective 1538 are all held on stages that allow for their controlled translation in three dimensions relative the window 1540. An X-Y stage 1544 is driven by a linear positioning stage (e.g., micrometer screw gauges), and controls an X-Y location of the arm adapter 1532, DOE 1536 and objective 1538, relative the window 1540. As illustrated in the front view 1510, a Z stage 1546 controls a Z location of the DOE 1536 and Objective 1538 relative to the window 1540. According to some embodiments, the window 1540 contacts the surface of the skin deforming the skin surface to conform with the shape of the window 1540. For example, a flat window flattens the surface of the skin and a convex window forms an indentation in the surface of the skin. According to some embodiments, pressure is applied by the window 1540 onto the surface of the skin. The pressure may provide a number of functions advantageous for laser treatment including evacuating blood and other competing targets (i.e., chromophores) from the treatment region; and, condensing the thickness of the skin, thereby shrinking the optical path length to treat deeper into the skin.

An ex vivo test was first performed with the optical system 1400 and handpiece 1500. Skin from a white (generally pigmentless) Yorkshire pig was used for the experiment. The Yorkshire pig was first tattooed with a melanin containing ink, such that artificial melanin macules were present in the dermis of the pig. A sample of skin having an artificial melanin macule in the dermis was used. With the exception of the artificial macule, generally no other pigment was present in the sample. The handpiece 1500 was placed on top of the sample, such that a protruding surface of the window sat flat upon and slightly pressed onto the sample. The Z location of the objective 1538 was varied in order to locate the focuses of the beamlets at two different depths (0.06 mm and 0.38 mm in air) away from the protruding face of the window 1540 (and into the sample). The distances of the focuses at two different depths from the window face was measured by first placing the window atop an acrylic block and firing a laser pulse into the acrylic block causing disruptions in the acrylic at the focuses. The distance from the top face of the acrylic block to the middle of the disruptions was measured using a depth measuring microscope and a 20× objective.

Figure 16A:
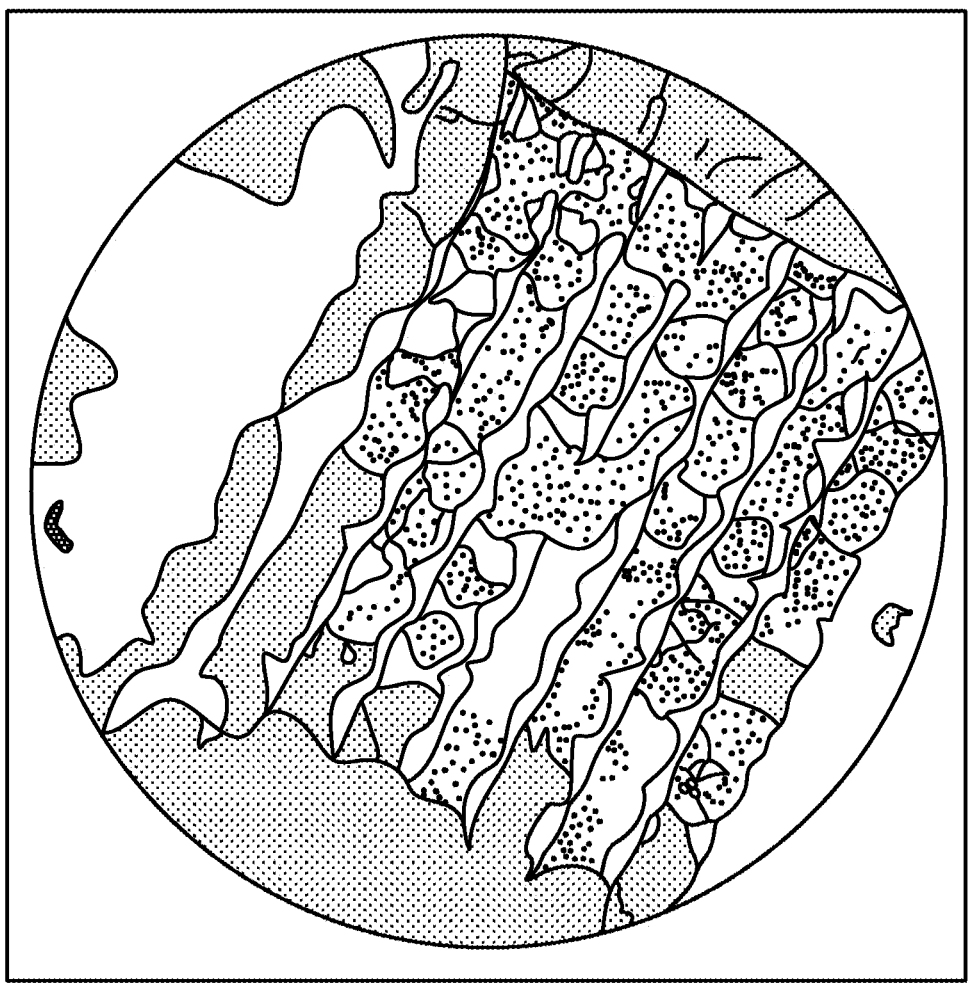
FIG. 16A illustrates an image of an array of disruptions formed in acrylic observed through a microscope.
Figure 16B:
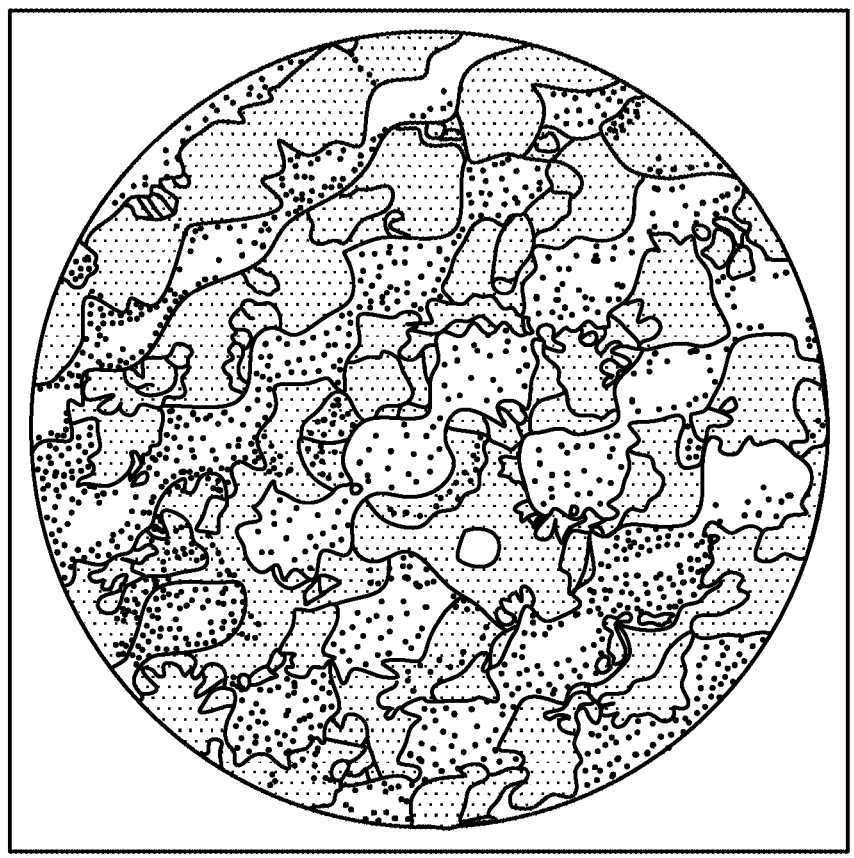
FIG. 16B illustrates an image of an array of disruptions formed in acrylic observed through a microscope.

FIG. 16A illustrates an image of an array of disruptions formed in acrylic observed through a microscope. The laser was fired (typically one laser pulse at a time) into the sample at locations in the sample containing the artificial macule (and its dermal pigment), and locations of sample that did not contain the artificial macules. One or more ND filters were used to attenuate the energy of the laser pulse. The total optical density (OD) of the ND filter's attenuation was chosen from 2, 2.2, 2.6, and 3. Losses through the system resulted in a measured pulse energy of 36mJ when an OD of 1 was used. The pulse energies corresponding with 2, 2.2, 2.6 and 3 values of OD are estimated to be 3.6mJ, 2.3mJ, 0.9mJ, and 0.036mJ, respectively. The presence or absence of a plasma was observed and recorded after each pulse. Table 1 below shows the results:

TABLE 1

| OD (—) | PULSE ENERGY (mJ) | Z LOCATION OF FOCUS IN SKIN (mm) | DERMIS PIGMENT (YES/NO) | PLASMA PRESENT (YES/NO) |
|---|---|---|---|---|
| 2 | 3.6 | 0.377 | NO | YES |
| 2 | 3.6 | 0.377 | YES | YES |
| 2.2 | 2.3 | 0.377 | NO | NO |
| 2.2 | 2.3 | 0.377 | YES | YES |
| 2.6 | 0.9 | 0.056 | NO | YES |
| 2.6 | 0.9 | 0.056 | YES | YES |
| 3 | 0.036 | 0.056 | NO | NO |
| 3 | 0.036 | 0.056 | YES | NO |

At a depth of 0.06 mm a plasma is formed (likely in the epidermis) with an OD of 2.6, and no plasma is formed with an OD of 3. There was no difference in plasma formation at this depth because of dermal pigment. At a depth of 0.38 mm, a plasma is formed in both pigmented and pigmentless dermis with an OD of 2; and a plasma is selectively formed only in the pigmented dermis at an OD of 2.2.

System 1400 and handpiece 1500 were used on a dark female Yucatan pig, who was selected based upon her skin type. The handpiece 1500 was placed atop the pig and the laser was operated at 1 HZ. In between pulses, the objective 1538 and DOE 1536 were scanned along the X-Y axes at a rate of 0.5 mm per pulse in a raster pattern. A number of passes were performed with the depth of focuses varied between 0.08 mm, 0.28, 0.48, 0.68 and 0.88 mm. Optical densities of 2 and 2.2 were used. Table 2 below describes treatment parameters used:

TABLE 2

| Treatment Site | OD | Treatment Region |
|---|---|---|
| M1 | 2.0 | 0.080 mm - single line |
| M2 | 2.0 | 0.080 mm - multiple lines |
| M3 | 2.2 | 0.080 mm |
| M4 | 2.0 | 0.080 mm |
| M5 | 2.0 | 0.080 + 0.200 mm |
| M6 | 2.0 | 0.080 + 0.400 mm |
| M7 | 2.0 | 0.080 + 0.600 mm |
| M8 | 2.0 | 0.080 + 0.800 mm |

Figure 17:
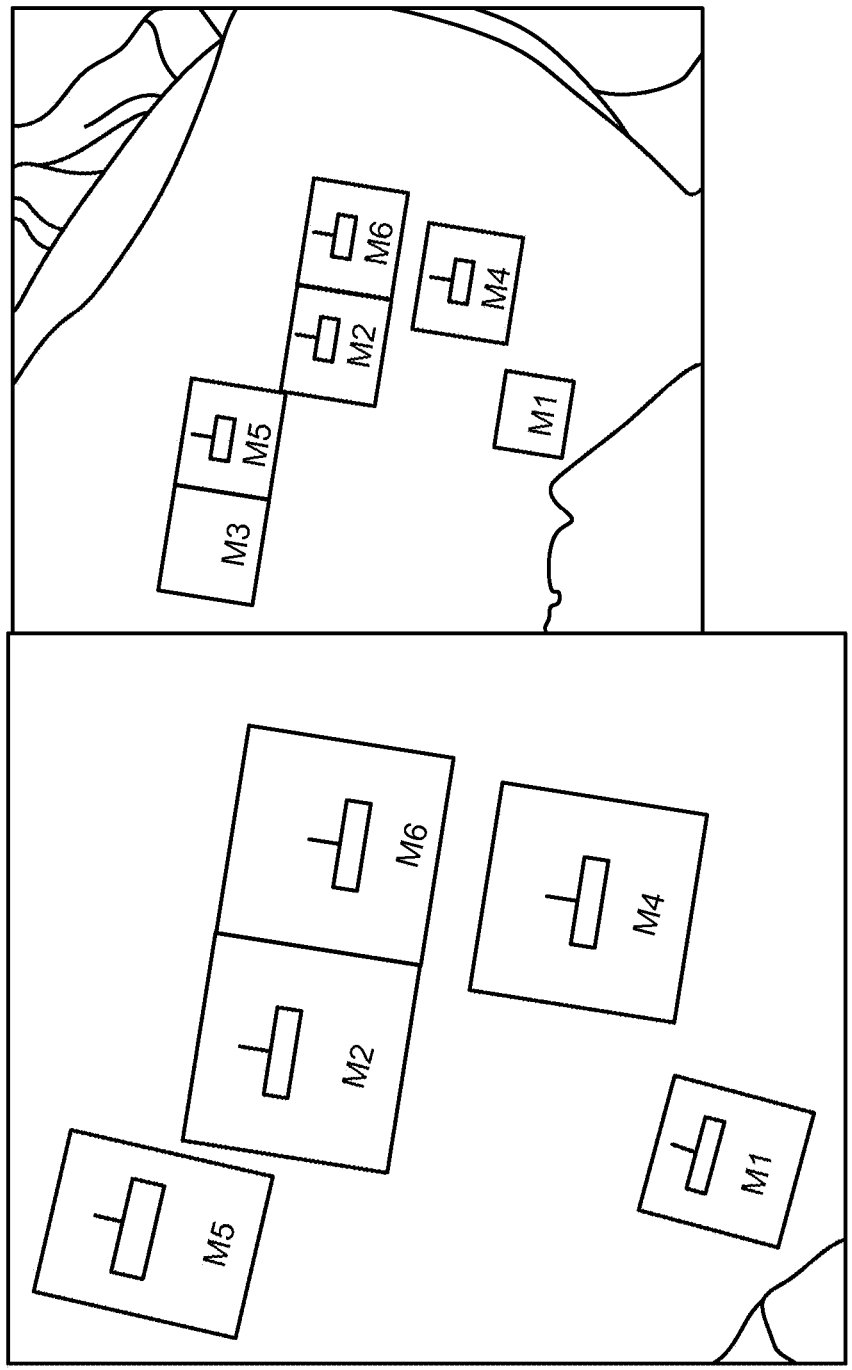
FIG. 17 illustrates images of treatment sites using the optical system in FIG. 14 and the handpiece in FIG. 15.
Figure 18A:
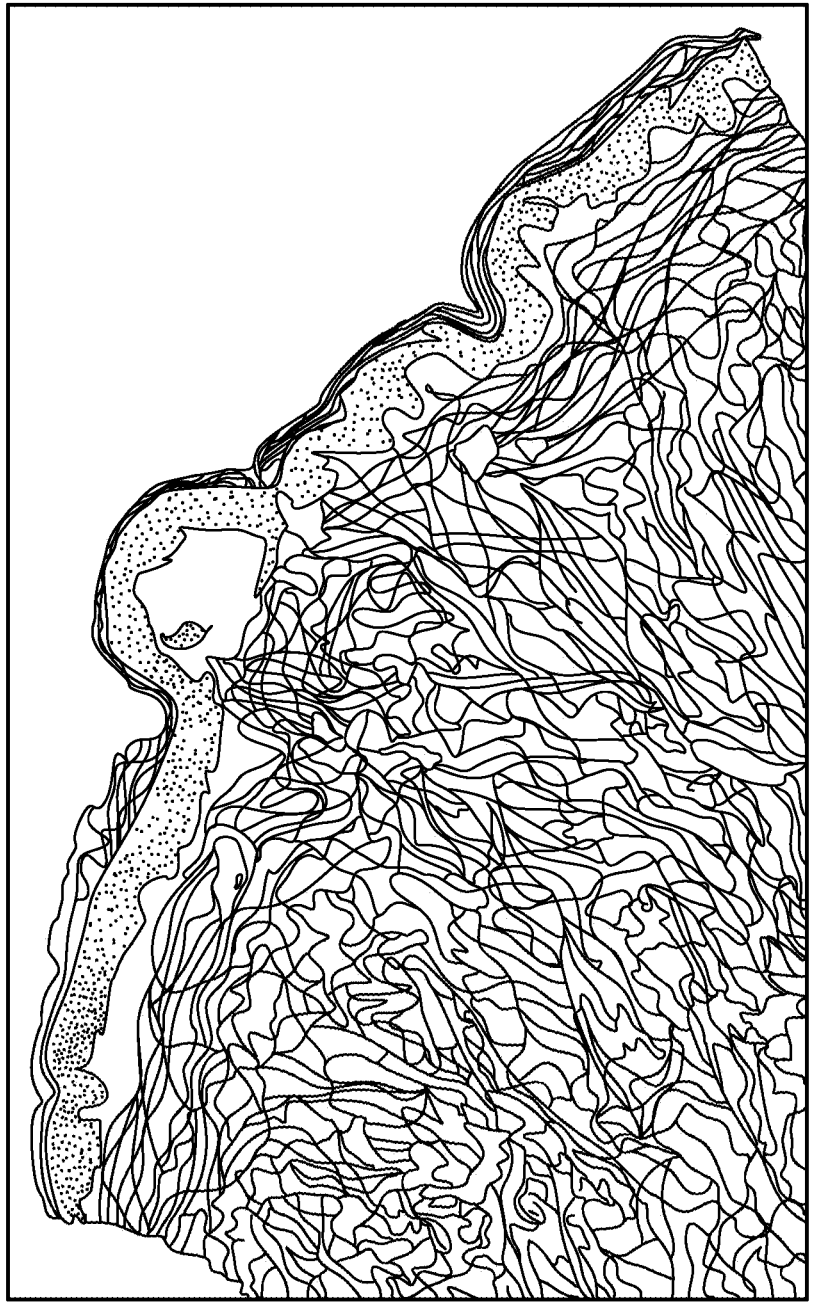
FIG. 18A illustrates a histology taken from treatment site M1 in FIG. 17.
Figure 18B:
FIG. 18B illustrates a histology taken from treatment site M6 in FIG. 17.
Figure 18C:
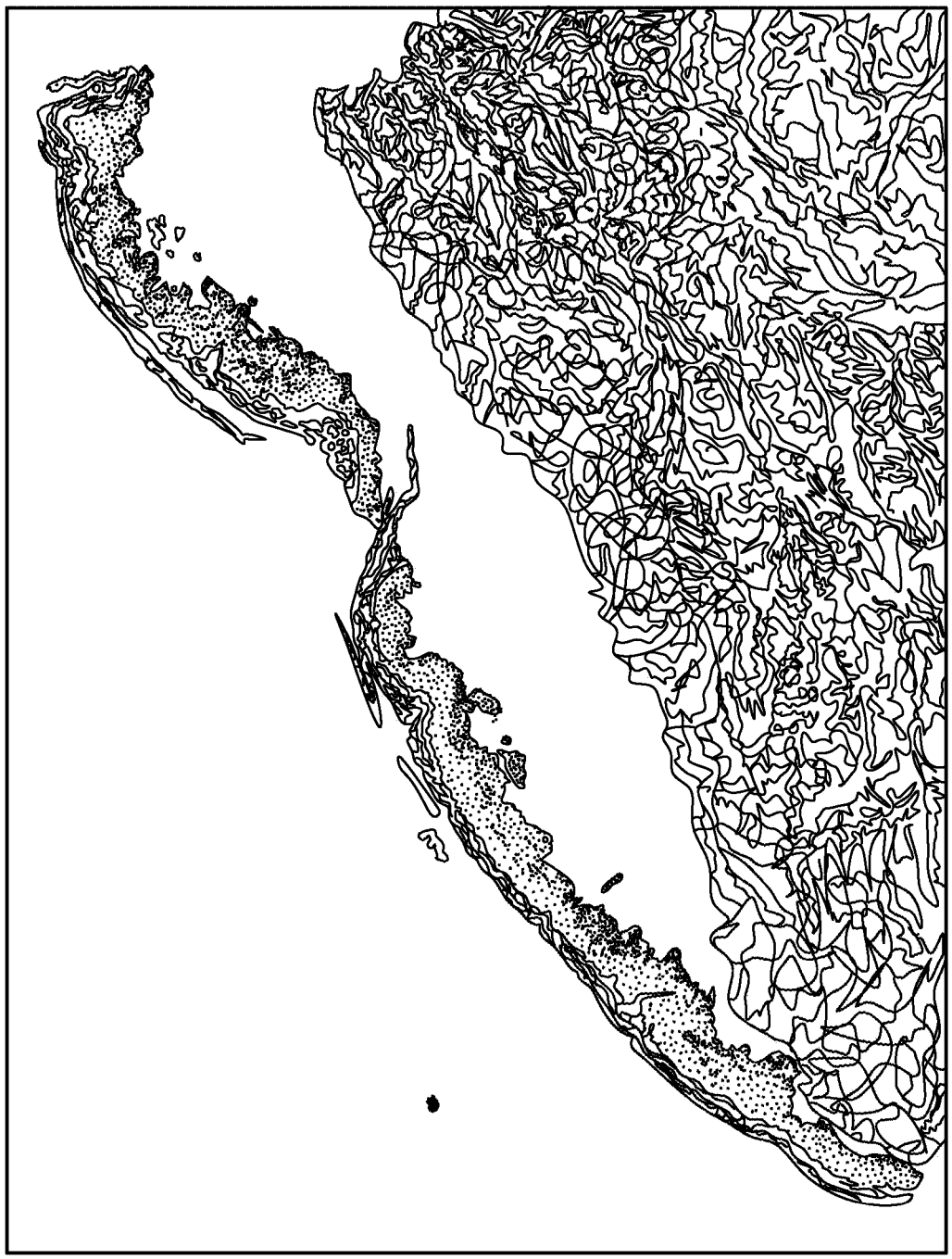
FIG. 18C illustrates a histology taken from treatment site M8 in FIG. 17.

FIG. 17 illustrates images of treatment sites using the optical system 1400 and the handpiece 1500. As shown in treatment site M3, an OD of 2.2 even at a depth as shallow as 0.08 mm in a dark skin big was unable to produce a cavitation and whitening in the pig. Cavitation and whitening were present in all other treatment sites, with relatively less cavitation present in deeper treatments, such as M7 and M8. Histological samples taken from treatment sites M1, M6 and M8 are shown in FIGS. 18A, 18B, and 18C respectively.

According to some embodiments, at least one of the diffractive beam splitter 402, the diffractive plate 902 and/or the diffractive element 1002 are produced by manufacturing processes including at least one of photolithography and diamond turning. According to some embodiments, at least one of the diffractive beam splitter 402, the diffractive plate 902, and/or the diffractive element 1002 are collocated on a single optical substrate. According to still other embodiments, at least one of the diffractive beam splitter 402, the diffractive plate 902 and/or the diffractive element 1002 are collocated on a single optical surface. An embodiment found to whiten Porcine epidermal pigment includes a laser beam being generated from a Q-switched laser source (Q-SMART 450 from Quantel of Les Ulis Cedex—France) and attenuated by an ND filter of optical density 2. A 9×9 two-dimensional beam splitter (PN: MS-027-I-Y-A from HOLO/OR of Tel Aviv, Israel) splits the laser beam into 81 beamlets. The 81 beamlets are focused by an optical system having a numerical aperture (NA) of about 0.5, a backfocal distance of about 12 mm, and a focal plane location of about 0.10 mm into pig skin. The above embodiment and parameters were found in a pig study to provide cavitation and whitening in a young female Yucatan pig.

Table 3 below outlines parameters and ranges that are appropriate for practicing some embodiments of the disclosure.

TABLE 3

| Parameter | Minimum | Nominal | Maximum |
|---|---|---|---|
| Numerical Aperture (—) | 0.3 | 0.5 | 1.0 |
| No. Focuses (—) | 1 | 5 | 50 |
| Depth of Focus(es) (mm) | 0.001 | 0.1 | 1 |
| Mean Depth of Focus(es) below a Surface (mm) | 0.01 | 0.2 | 1 |
| Array Size (-X-) | 1 × 1 | 10 × 10 | 100 × 100 |
| Array Width (mm) | 0.05 | 0.5 | 5 |
| Separation Angle of Array (°) | 0.05 | 0.5 | 5 |

Figure 19:
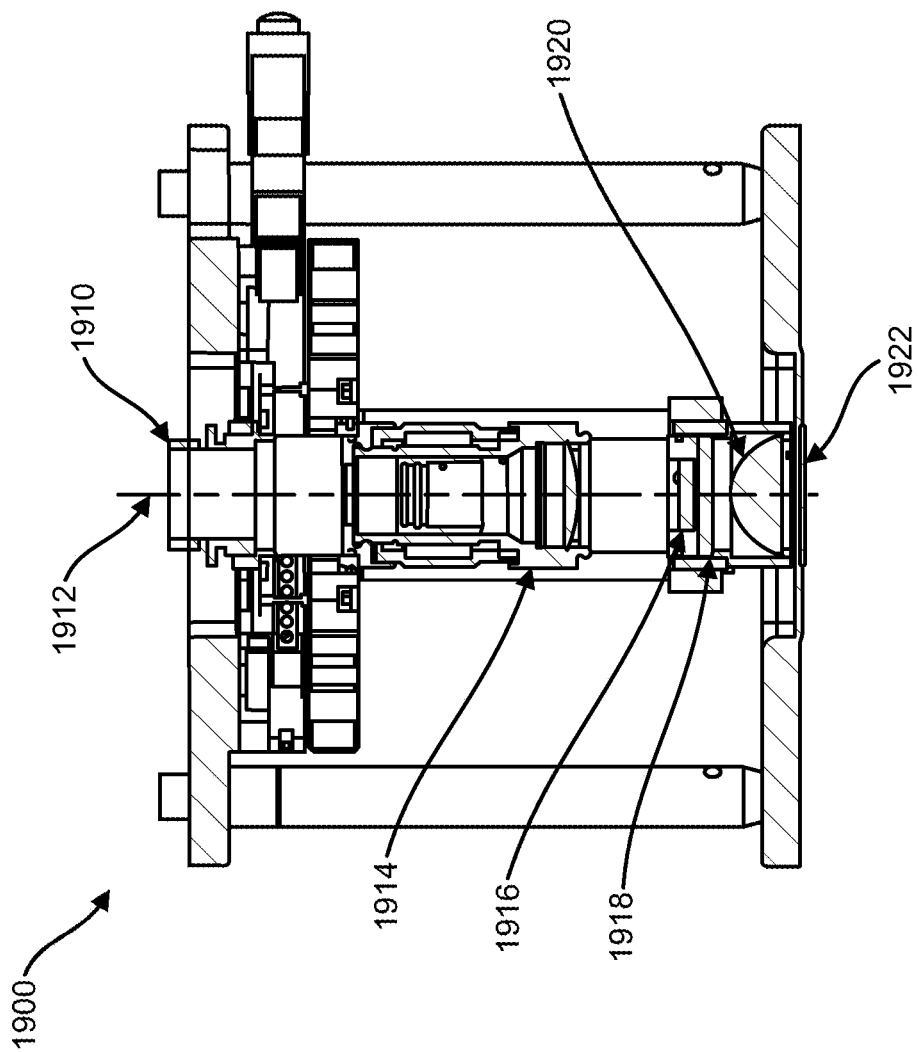
FIG. 19 illustrates a treatment system that includes diffractive optical elements.

A system was developed using diffractive optical elements (DOEs) and a Q-switched Nd:YAG laser (e.g. Quantel Q-Smart 450). Referring to FIG. 19, a handpiece 1900 is shown having an adapter 1910 for attaching to an articulating arm. A laser beam is directed generally along an optical axis 1912. A beam expander 1914 (e.g., Thorlabs Part No. BE02-UVB) increases the laser beam diameter two times to a diameter of about 14 mm. The laser beam is diffracted by a first DOE 1916, in this case a multi-focal element that produces 5 focuses (e.g., Holo/OR Part No. MF-001-I-Y-A). The multi-focal element separates the laser beam into 5 beamlets, each having a slightly different divergence. The beamlets are then diffracted by a second DOE 1918, in this case a 9×9 2D beam splitter (e.g., Holo/OR Part No. MS-027-I-Y-A). The second DOE diffracts each of the incoming 5 beamlets and diffracts them into 9×9 (or 81) sub-beamlets, each sub-beamlet having a slightly different tip and/or tilt gradient based upon the beam splitters separation angle (e.g., 0.5 degrees). The 5×9×9 sub-beamlets (or 405 sub-beamlets) are then brought to 405 focuses by an objective 1920 (e.g., Edmunds Optics Part No. 67-259). Finally, a window 1922 is located in an optical path between the 405 focuses and the objective 1920. An example window 1922 is Edmunds Optics Part No. 48-919. A nominal pitch between adjacent focuses belonging to the same 9×9 array is approximated by multiplying an effective focal length of the objective 1920 (e.g., 15 mm) by the sine of a separation angle of the 2D beam splitter (0.5°), or about 0.13 mm. A total nominal width of a 9×9 array is approximated by multiplying the nominal pitch by a number of points in the array minus one (e.g., 8), or about 1 mm.

Figure 20B:
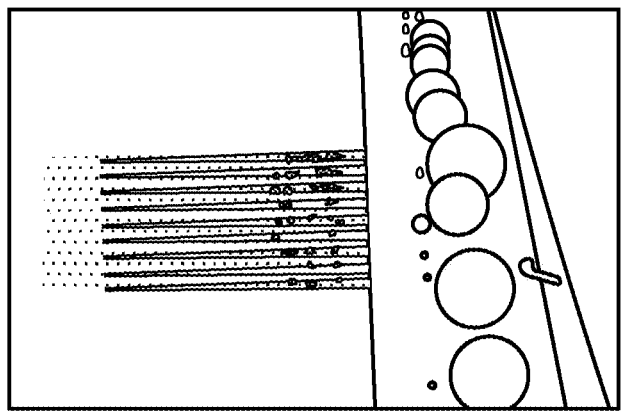
FIG. 20B illustrates a microscope image of another side view of the gray tinted acrylic block.
Figure 20A:
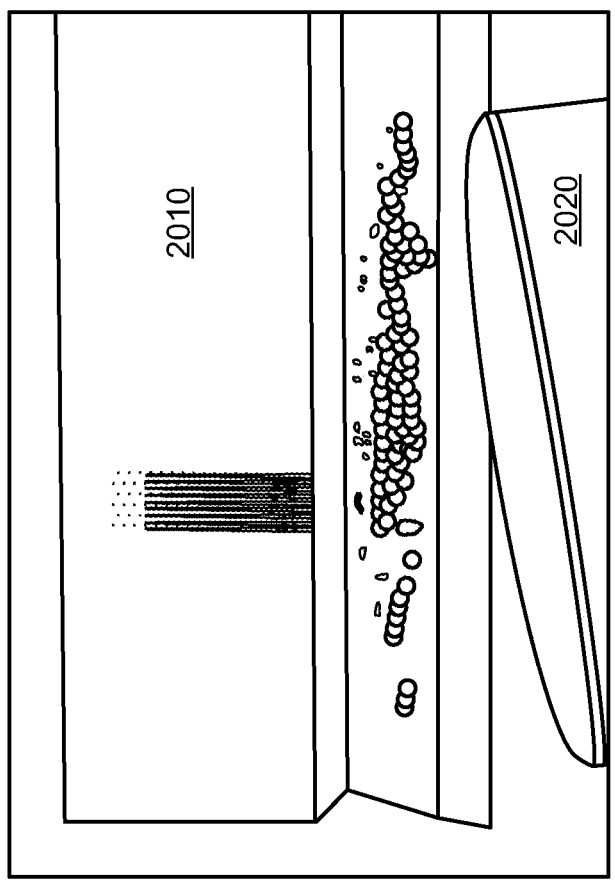
FIG. 20A illustrates a microscope image of a side view of the gray tinted acrylic block.
Figure 21A:
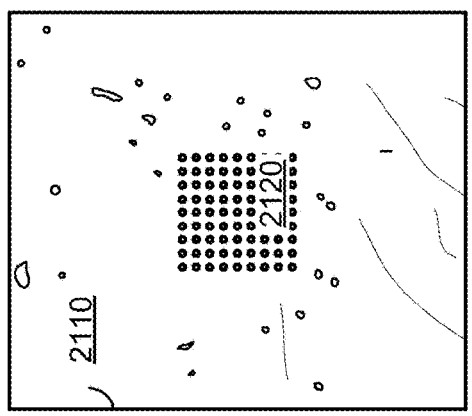
FIG. 21A illustrates a microscope image of a front view of the gray tinted acrylic block in FIG. 20A.
Figure 21B:
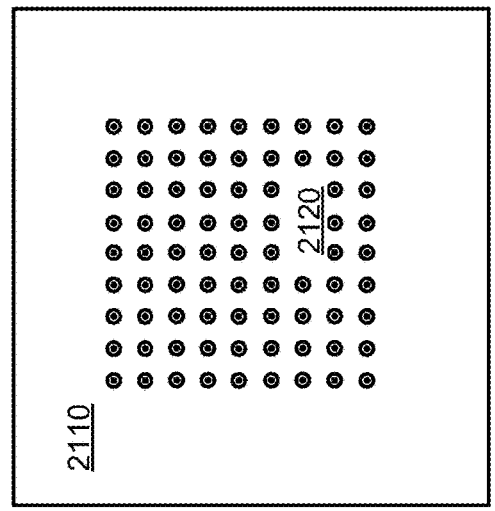
FIG. 21B illustrates a microscope image of a front view of the gray tinted acrylic block in FIG. 20A.

The system and handpiece 1900 were initially tested using gray tinted acrylic block. The acrylic was placed flat against the window 1922. The laser beam was attenuated by an optical density (OD) of 0.4. A first pulse was delivered to the acrylic to a depth of about 1.01 mm into the acrylic (at the shallowest). It was found in the acrylic the 5 focuses were close enough so that a single focal volume formed a single column of damage that resulted over the 9×9 2D array (instead of there being 5 discrete 9×9 arrays of damage at 5 discrete depths). The first laser pulse resulted in columns of damage that were generally 0.49 mm deep, such that the bottom of the columns was about 1.55 mm deep into the acrylic block. A location of the objective was adjusted and a second pulse was delivered to the acrylic block. The depth of damage resulting from the second pulse began generally at 0.48 mm and extend to a depth of 1.11 mm (about 0.63 mm deep columns of damage). FIGS. 20A-B show microscope images of a side view of the gray tinted acrylic block 2010. The block was illuminated by two fiber optic light sources directed from opposite sides transverse to the microscope optical path. One fiber optic light source 2020 is shown in FIG. 20A. Referring to FIG. 20B, 9 columns of damage 2030 are shown between the two dashed curves. It is believed that the dashed curves, representing the demarcation between ablated and non-ablated acrylic, are curved because of a field curvature of the objective. FIGS. 21A-B show microscope images of a front view of the gray tinted acrylic block 2110. A 9×9 array 2120 of columns of damage can be seen. This particular 9×9 array 2120 has no center column and therefore only has 80 columns instead of 81.

The system and handpiece 1900 were then used to perform an ex vivo treatment upon skin harvested from a white Yorkshire female pig. The laser had a 50 µS delay introduced to lower the energy per pulse and the beam was attenuated by an OD of 0.5. Pulse energy at these settings was approximately 108mJ per pulse. And, pulse duration at these settings was approximately 8 nS per pulse. Four skin samples were irradiated. A plasma was observed to occur with each laser pulse on each sample. Parameters associated with each sample are shown in Table 4 below:

TABLE 4

| Sample | Min. Depth of Focus (measured in air) (mm) | Max. Depth of Focus (measured in air) (mm) | Rep. Rate (Hz) | Scan Rate (mm/S) | Scan Pattern |
|---|---|---|---|---|---|
| 1 | 0.19 | 0.63 | 1 | 0.5 | Raster |
| 2 | 0.34 | 0.79 | 1 | 0.5 | Raster |
| 3 | 0.03 | 0.50 | 1 | 0.5 | Raster |

As scan rate was about 0.5 mm in both X-Y and the repetition rate was about 1 Hz, it is assumed that every area treated (not on the periphery of the treatment) was treated 4 times by the 1×1 mm array. Therefore, an effective treatment pitch was about half that of the nominal 9×9 array, 0.07 mm. Said another way, damage resulting from treatment was expected to occur about every 0.07 mm in X and Y directions.

Sparks occurred during irradiation of the samples concurrent with laser pulses, with more intense sparks seen with more superficial depths (e.g., Sample 3). After irradiation the surface of the samples was inspected under microscope, biopsied and sent for histology. No damage on the surface of the tissue was observed under microscopic examination for any of the samples. The presence of sparks (indicating plasma) and the lack of damage to the skin surfaces implies that ablative damage was confined to within the tissue and beneath an epidermal layer in the tissue.

Figures 22C, 22D:
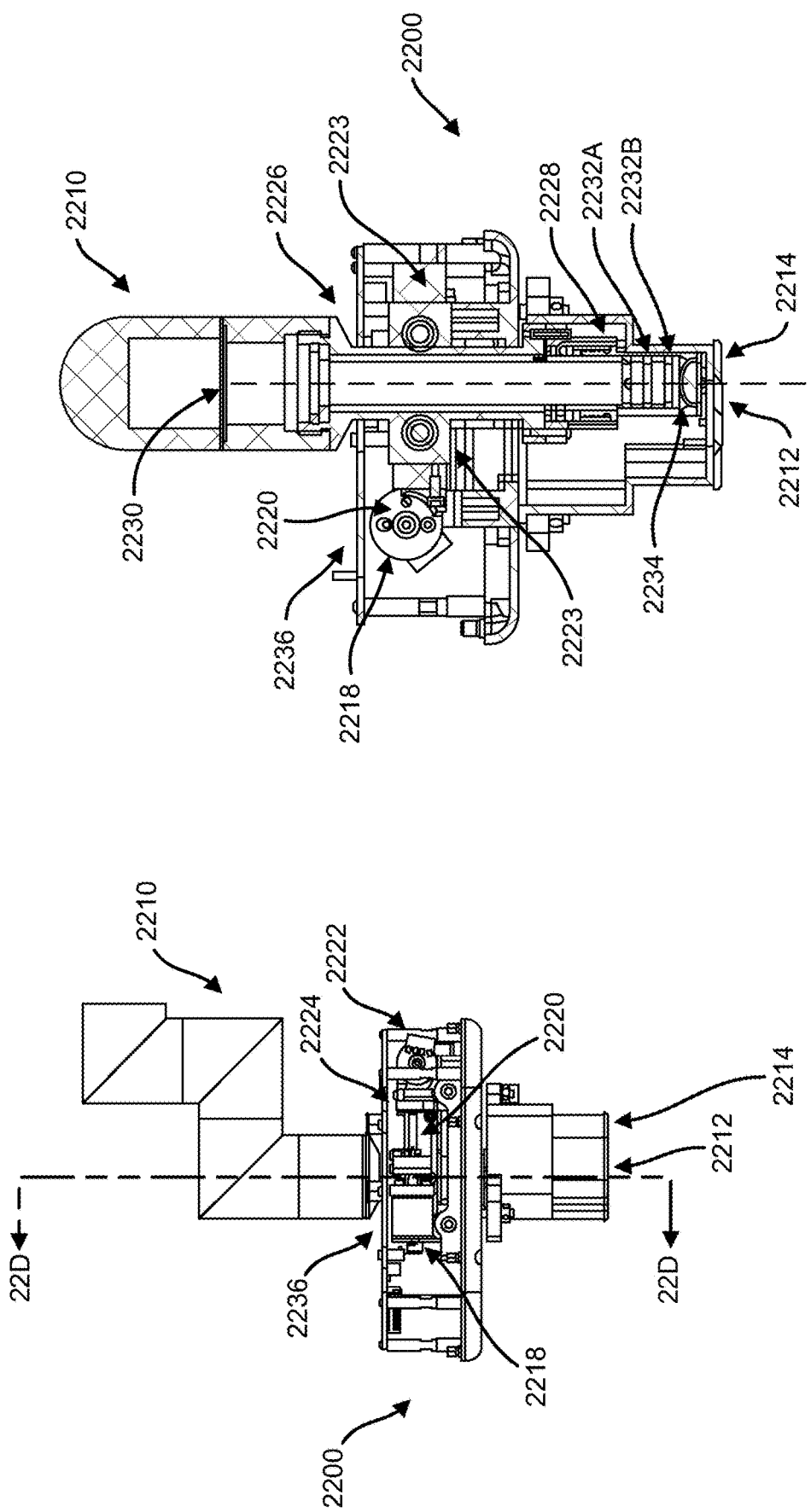
FIG. 22C illustrates a front view of the treatment system handpiece in FIG. 22A shown without a cover.
FIG. 22D illustrates a cross-sectional view of the treatment system handpiece in FIG. 22A shown without a cover.

FIGS. 22A-D illustrate an exemplary handpiece 2200 according to some embodiments. FIG. 22A illustrates a front view of the handpiece 2200 while FIG. 22B illustrates a bottom view of the handpiece 2200. An articulating arm 2210 directs a laser beam from a console that includes a laser source (not shown) into the handpiece 2200. The handpiece 2200 includes a window 2212, which can be generally transmissive to the laser beam. A person skilled in the art will understand that a variety of window materials can be used, but exemplary window materials include sapphire and quartz. According to some embodiments, a contact sensor 2214, which can include one or more capacitive sensors, can detect when the window 2212 is in contact with a tissue. A person skilled in the art will understand that the handpiece 2200 can include a cover 2216 that encapsulates the various components of the handpiece 2200.

FIG. 22C illustrates a front view of the handpiece 2200 without the cover 2216. FIG. 22D illustrates a cross-sectional view taken along line 22D-22D in FIG. 22C. Referring now to FIGS. 22C and 22D, a first motor 2218 (e.g., stepper motor) drives a first lead screw 2220 that moves a first stage 2223 along a first axis. A second motor 2222 drives a second lead screw that moves a second stage 2224 along a second axis (e.g., generally orthogonal to the first axis). The first motor 2218 and the first lead screw 2220 are mounted to the second stage 2224, so that movement of the second stage 2224 moves the first motor 2218 and the first lead screw 2220 along the second axis. The first stage 2223 is attached to a lens tube 2226, so movement of the first stage 2223 along the first axis results in a movement of the lens tube 2226 (or movement of the articulating arm 2210 coupled to the lens tube 2226) along the first axis. Movement of the first stage can also lead to the movement of diffractive optical elements (DOE) 2232A and 2232B and focus optics 2234. Furthermore, as the first motor 2218 and first lead screw 2220 are attached to the second stage 2224, movement of the second stage 2224 along the second axis results in a movement of the lens tube 2226 along the second axis. The lens tube 2226 is attached at an optical output of the articulating arm 2210 at a first side and is attached to a depth stage 2228 at a second side. An optical axis 2230 can be parallel to the cylindrical axis of the lens tube 2226. One or more diffractive optical elements (DOEs) 2232A-B can be arranged along the optical axis 2230 (e.g., coupled to the lens tube 2226). According to some embodiments, a first DOE 2232A comprises a multi-focus element as described above, and a second DOE 2232B comprises a two-dimensional beam splitter (e.g., diffractive beam splitter) as described above. A focus optic 2234 is mounted down beam along the optical axis 2230 within the depth stage 2228 (e.g., coupled to the lens tube 2226). Typically, the one or more DOEs 2232A-B split the laser beam into a plurality of beamlets. The focus optic 2234 can focus one or more of the plurality of beamlets (e.g., to one or more focal regions). The depth stage 2228 moves the focus optic 2234 up and down along the optical axis 2230, thereby moving a depth of the plurality of focal regions along the optical axis 2230. A motor controller 2236 can control one or more of the first motor 2218 and the second motor 2222. According to some embodiments, a first position sensor can measure a position of the first stage 2223 and a second position sensor can measure a position of the second stage 2224. Examples of position sensors include linear encoders, rotation encoders, and home sensors. Additionally, in some implementations, the first motor 2218 and/or the second motor 2222 comprise a stepper motor and position of the first and/or second stage can be inferred by counting steps. According to some embodiments, the motor controller 2236 is communicative with a laser controller (not shown) that controls one or more laser parameters. According to some embodiments, the laser controller controls at least one of: pulse duration, pulse energy, and laser repetition rate. According to some embodiments, an attenuator can be placed in the beam path and an attenuator controller can control the level of attenuation. In some embodiments, the attenuator can include an attenuator controller that is communicative with the motor controller 2236. According to some embodiments, one or more of the laser controller, the attenuator controller, and the motor controller can work in conjunction to ensure safe and effective treatment. For example, in some implementations, the motor controller can track the position of both the first stage 2223 and the second stage 2224 and can interrupt the laser if either stage is out of a predetermined range. This safety feature can prevent the system from excessively irradiating a given location (e.g., leading to tissue damage).

The handpiece 2200 as described in reference to FIGS. 22A-D, is optically coupled via the articulating arm 2210 to a Quantel Q-Smart 400 Laser, which delivers a laser beam having a nominal 400mJ laser pulse at a 6 nS pulse duration and a repetition rate of 20 Hz. Pulse duration and pulse energy of the laser beam is interdependently controlled by a Q-Switch delay parameter. An attenuator is located in the path of the laser beam between the laser source and the handpiece 2200. The attenuator comprises a PowerXP-Compact Motorized Attenuator from Altechna of Vilnius, Lithuania. The attenuator includes an attenuator controller and allows for the pulse energy laser of the laser beam to be further controlled independently of the pulse duration. Laser parameters, such as pulse duration, pulse energy and peak power were found experimentally when adjusting Q-switch delay and attenuation level. The resulting laser parameters are summarized in Table 5 below for reference:

TABLE 5

| Delay (uS) | Pulse Energy w/ 0.5OD Attenuation (mJ) | Pulse Energy No Attenuation (mJ) | Pulse Energy at End of Arm (mJ) | Pulse Duration (ns) | Peak power (MW) |
|---|---|---|---|---|---|
| 0 | 139 | 420.1 | 386.3 | 7.2 | 53.7 |
| 50 | 108 | 326.4 | 300.2 | 8 | 37.5 |
| 100 | 63 | 190.4 | 175.1 | 11 | 15.9 |
| 120 | 45 | 136.0 | 125.1 | 13.5 | 9.3 |
| 140 | 33 | 99.7 | 91.7 | 15.7 | 5.8 |
| 160 | 22.4 | 67.7 | 62.3 | 18 | 3.5 |

Treatment of some skin conditions, for example dermal pigmentary conditions like Melasma or Post-Inflammatory Hyperpigmentation (PIH), require that a high energy density be delivered to a target-layer of tissue (e.g., the dermis) while an ante-layer of tissue (e.g., the epidermis) experiences a lower energy density. It is desirable that the high energy density within the target-layer be above a therapeutic threshold known to cause a therapeutic effect (e.g., thermionic plasma or thermal disruption of targets within a target). If the energy density in the target-layer is below this therapeutic threshold no therapeutic effect and therefore no treatment will occur. Furthermore, it is desirable that the lower energy density experienced by target-layer (e.g., the epidermis) be below a deleterious threshold found to cause deleterious effects (e.g., increased melanin production within melanocytes). If the energy density within the ante-layer is greater than this deleterious threshold, deleterious effects will manifest within the ante-layer (e.g., melanin production can increase [for example, tanning will occur]) and the condition is likely to worsen. The therapeutic threshold and/or the deleterious threshold can be dependent upon a number of factors, for example, patient skin type (e.g., melanin content), energy, wavelength, pulse energy, and pulse duration of the laser beam, and cooling of the target tissue. For this reason, a parameter, such as pulse energy, can be selected through titration on an individual patient until laser beam having and energy density above the therapeutic threshold is reached within a target in the target-layer and the energy density of the laser beam is below the deleterious threshold in the ante-layer. For there to be an adequate difference between the energy densities of the laser beam in the ante-layer and the target-layer, the laser beam must converge as it propagates within the tissue from the ante-layer of tissue to the target-layer of tissue. A parameter that controls a rate of convergence of the laser beam is numerical aperture (NA). The greater the NA the greater the rate of convergence; and therefore, the greater the difference between the ante-layer energy density and the target-layer energy density. Unfortunately, many commonly treated tissues (e.g., skin) are a turbid medium (e.g., they scatter light like a cloud or a glass of milk). Therefore, as the laser beam propagates within skin it can aberrate and its beam size can bloom, increasing its area and reducing its energy density (and reducing its difference in ante-layer and target-layer energy density). In some embodiments, the target-layer of tissue and the ante-layer of tissue are not necessarily different tissues. Said another way, in some embodiments, the target-layer and the ante-layer are both within a single tissue type (e.g., epidermis). Use of a high-quality laser beam (e.g., $M^2 <= 2$) along with a diffraction limited focusing system having a high NA (e.g., $NA >= 0.3$) can provide a difference between energy density in the epidermis and the dermis that can allow for selective treatment of dermal conditions in some skin types. However, treating large lesions clinically with a high NA focus and a high-quality beam introduces new challenges.

A high NA focus system requires a relatively short focal length. For example, an NA of 0.5 corresponds to a focal length equal to beam diameter of the laser beam (e.g., a beam diameter of 8 mm and a focal length of 8 mm). A high NA focus system can also produce a relatively small focal region (e.g., 1-100 micrometers in diameter). Treatment can occur within and directly proximal to the focal region, and many focal regions can be delivered to treat the lesion. Lesions are known to range in size (e.g., they can be the size of a bottle cap). As described herein, a diffractive optic may be used to produce an array of focuses thereby increasing the area that is treated. For a lesion having a size of a bottle cap, an array of focuses the size of the bottle cap can be desired. However, as described above, array width can be approximated by multiplying full angle of the array and focal length of the focusing system. As the high NA requirement constrains the optical system to a relatively short focal length, the full angle needed to achieve a large array can become very large. Continuing with the example, a small lesion the size of a bottle cap (e.g., 26 mm in diameter), an 8 mm diameter beam with a NA of 0.5 requires an 8 mm focal length. An array of focuses 26 mm in diameter produced with an 8 mm focal length system would require a full angle of almost 120°. As described above, a beamlet at the periphery of the array would pass through the focusing system at half the full angle. Beamlets passing off-axis through a focusing system are known to result in aberrations (e.g., coma, astigmatism, and field curvature aberrations). However, high beam quality or low aberrations are required to ensure a difference in energy density between the epidermis and the dermis, and thereby provide desirable energy density in epidermis and dermis. For this reason, lesion sized arrays with a high NA and high beam quality may not possible. Aberrations can be reduced with arrays having a full angle smaller than 20° and preferably smaller than 5°. In order to provide a clinically viable treatment for dermal pigmentary conditions, it is necessary to treat lesions of all sizes using an array of focuses having a width much smaller than that of the lesion.

Figure 23A:
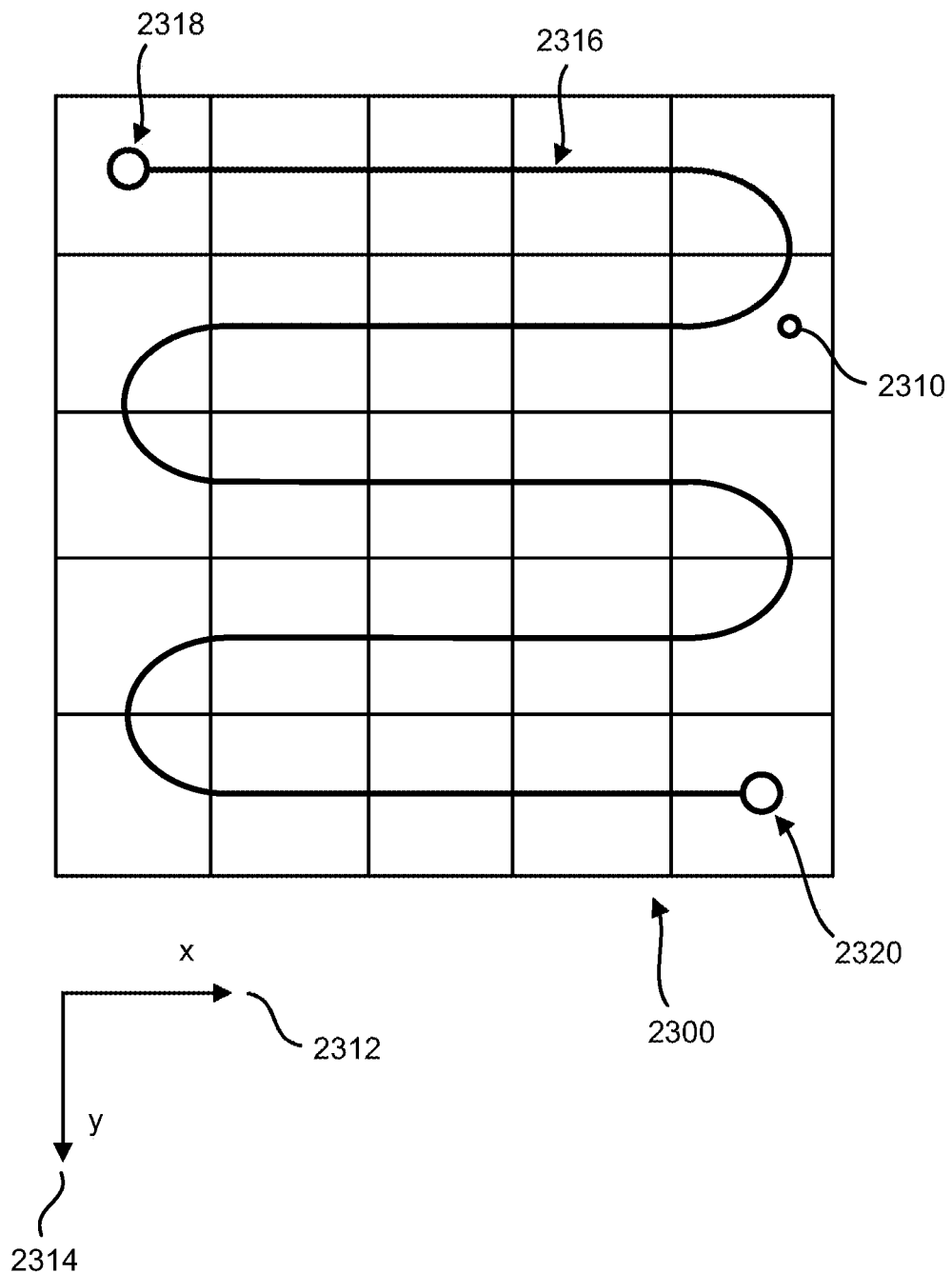
FIG. 23A is a schematic representation of an exemplary scanned treatment layer.

One or more scans 2300 may be used to treat a lesion with an array of focuses smaller than the lesion. An exemplary layer scan 2300 is schematically represented in FIG. 23A. The layer scan 2300 comprises a plurality of focal arrays 2310. Each focal array 2310 comprises a plurality of focuses and is formed by an individual laser pulse. As described above the focal array 2310 can be any one of: a one-dimensional array, a two-dimensional array, and a three-dimensional array. The layer scan 2300 is two-dimensional and can be performed over a first axis 2312 and a second axis 2314 (e.g., by translating a laser beam along the first axis 2312 and/or a second axis 2314). According to some embodiments, the layer scan 2300 is performed in a boustrophedon pattern 2316 (e.g., a raster pattern). In this case, the layer scan 2300 is started at a first corner 2318 and is finished at a second corner 2320 and consecutive focal arrays 2310 are generated consecutively (e.g., temporally) and can be physically adjacent. According to some embodiments, it can be advantageous to have temporally consecutive focal arrays 2310 non-adjacent to one another, for example to reduce bulk heating over a single location. According to some embodiments, a treatment scan 2350 comprises multiple layer scans 2300.

Figure 23B:
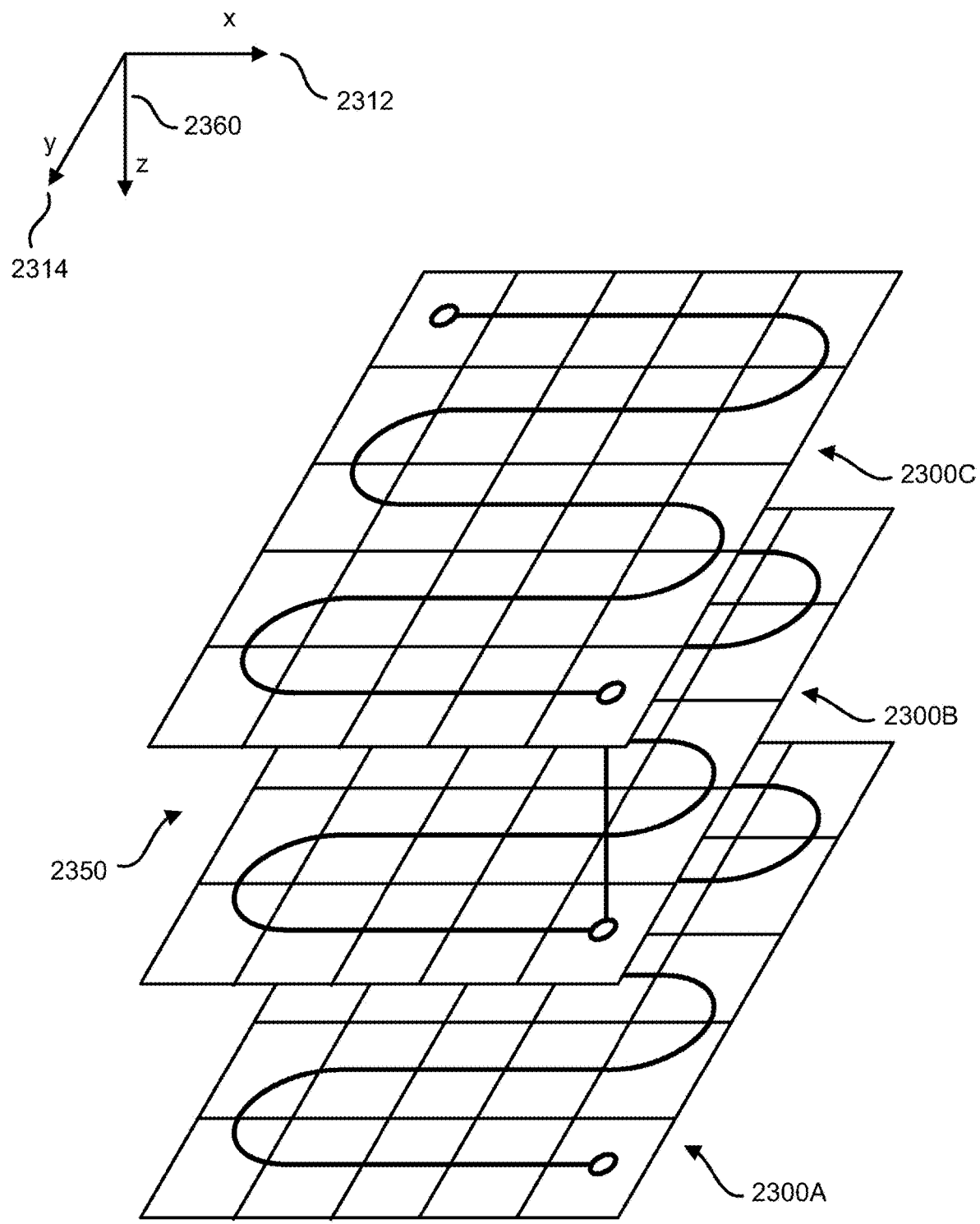
FIG. 23B is a schematic representation of an exemplary scanned treatment comprising multiple layers.

A treatment scan 2350 comprising three layer scans 2300A-C is schematically represented in FIG. 23B. After a first layer scan 2300A the focal array depth is moved along a third axis 2360 and a second layer scan 2300B is performed. After the second layer scan 2300B the focal array depth is moved again along the third axis 2360 and a third layer scan is 2300C is performed.

The system as described in reference to FIG. 22 was used to treat fresh Yucatan porcine skin according to the layer scan 2300 described in FIG. 23A. The Yucatan porcine skin was harvested prior on the day of the scan from a young Yucantan pig. Prior to treatment, laser parameters were found that selectively caused thermionic plasma in pigmented tissue and no plasma in largely pigmentless tissue. A 2D beam splitting DOE was used that formed a 9×9 array of focuses (with the center focus, absent a total of 80 focuses are formed). The 9×9 array had a size found to be approximately 0.6 mm square. The Yucatan pig tissue was treated by firing the laser at a first location, scanning the objective to a second location generally 0.6 mm away from the first location, firing the laser, and repeating in a boustrophedon pattern until a large enough scan layer for biopsy was treated. Parameters used during treatment and observation made during treatment are shown in Table 6 below:

TABLE 6

| Sample | Sample Type | Q-switch Delay (uS) | Z Stage Setting (um) | Approx. Focal Depth (um) | Plasma Visible During Treatment | Whitening Post Treatment |
|---|---|---|---|---|---|---|
| 1 | Treated | 120 | 870 | 200 | Plasma | No |
| 2 | Treated | 150 | 1500 | 830 | No | No |
| 3 | Treated | 150 | 800 | 130 | Plasma | Yes |
| 4 | Control | N/A | N/A | N/A | N/A | N/A |

Figure 23C:
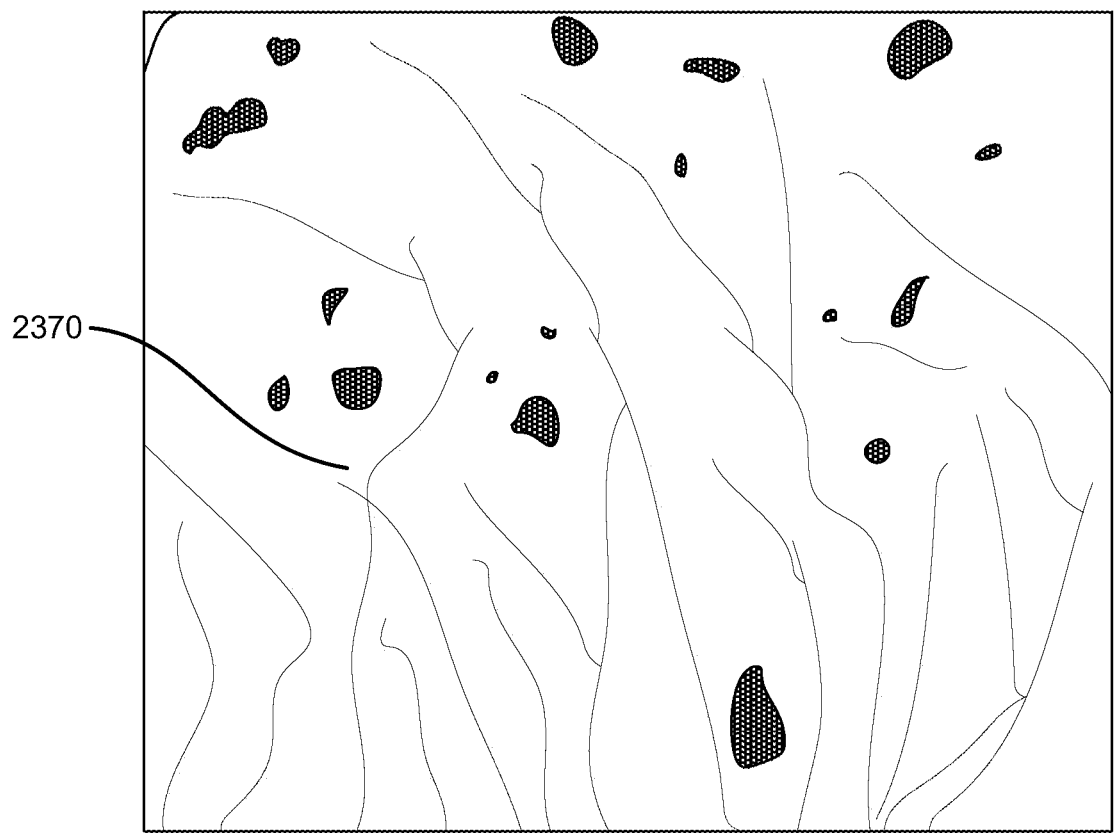
FIG. 23C is an image of an exemplary fresh Yucatan pig skin after treatment.

As can be seen from the observations in the table above, focusing the array of focuses deeper into the skin (e.g., well below the melanin containing epidermis) resulted in little to no thermionic plasma at the same laser settings. And, more superficial treatment of the tissue (e.g., where the array of focuses was generally at the same depth as the melanocyte containing basal layer of the epidermis) resulted in a visible whitening of the tissue post-treatment (SAMPLE 3). An image showing whitening 2370 of SAMPLE 3 post-treatment is shown in FIG. 23C.

Figure 24A:
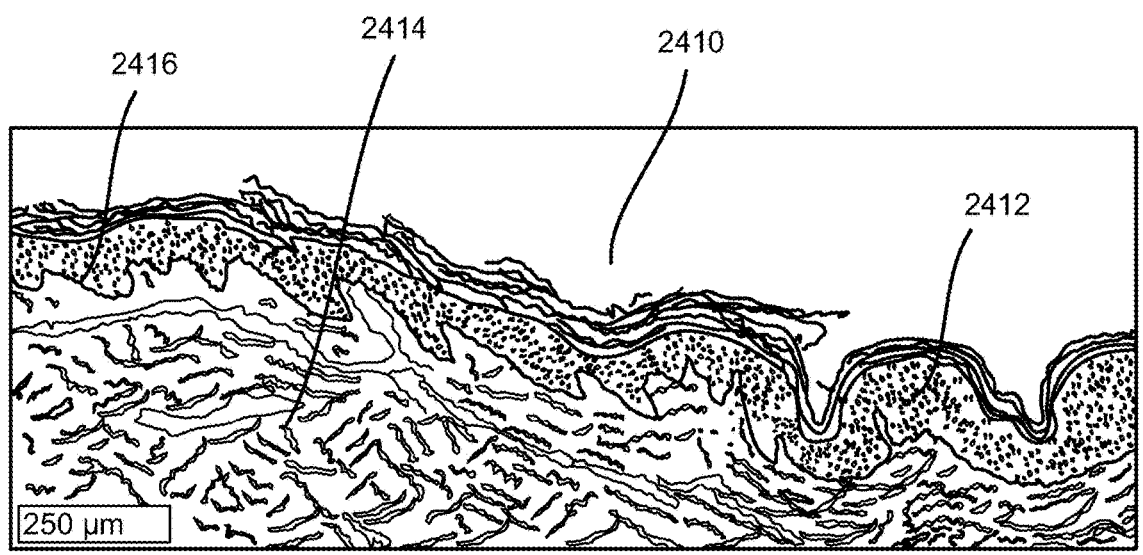
FIG. 24A shows an image of an exemplary histology of a control Porcine skin sample stained with Fontana-Mason.
Figure 24B:
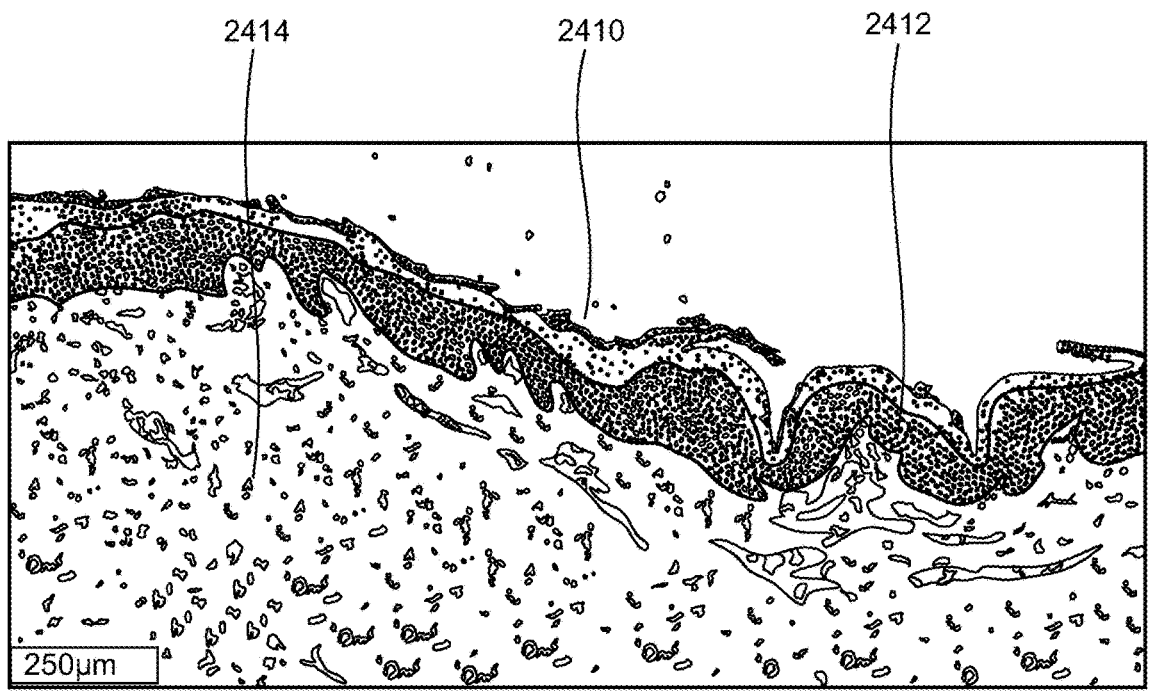
FIG. 24B shows an image of an exemplary histology of a control Porcine skin sample stained with TUNEL.
Figure 24C:
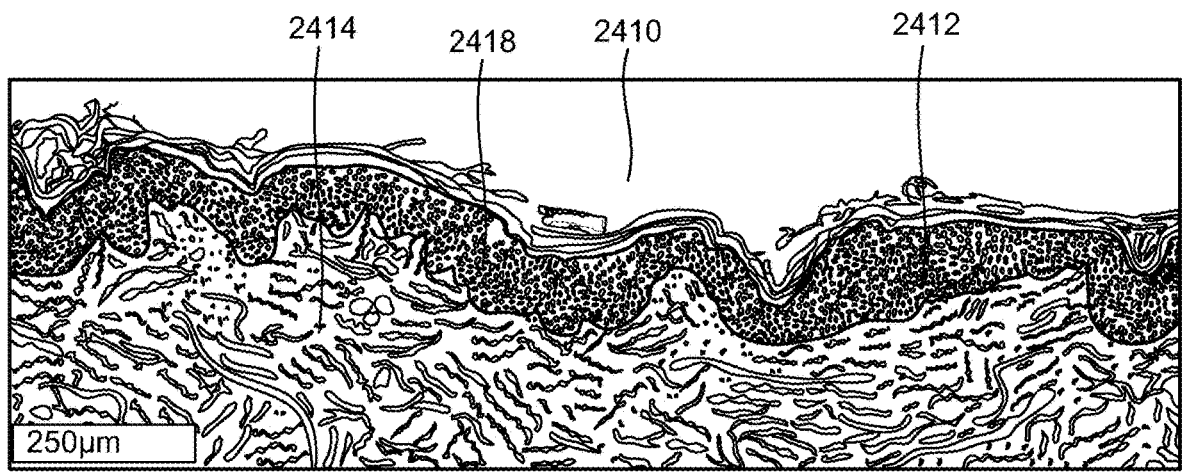
FIG. 24C shows an image of an exemplary histology of a Porcine skin sample taken after ex vivo treatment and stained with Fontana-Mason.
Figure 24D:
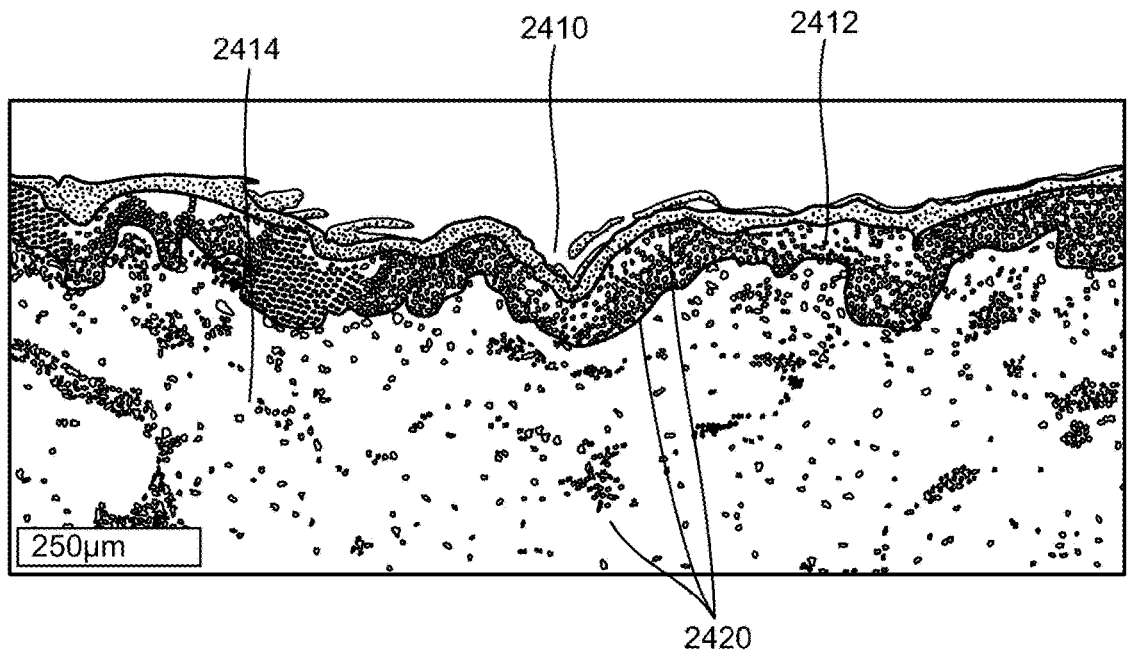
FIG. 24D shows an image of an exemplary histology of a Porcine skin sample taken after ex vivo treatment and stained with TUNEL.
Figure 24E:
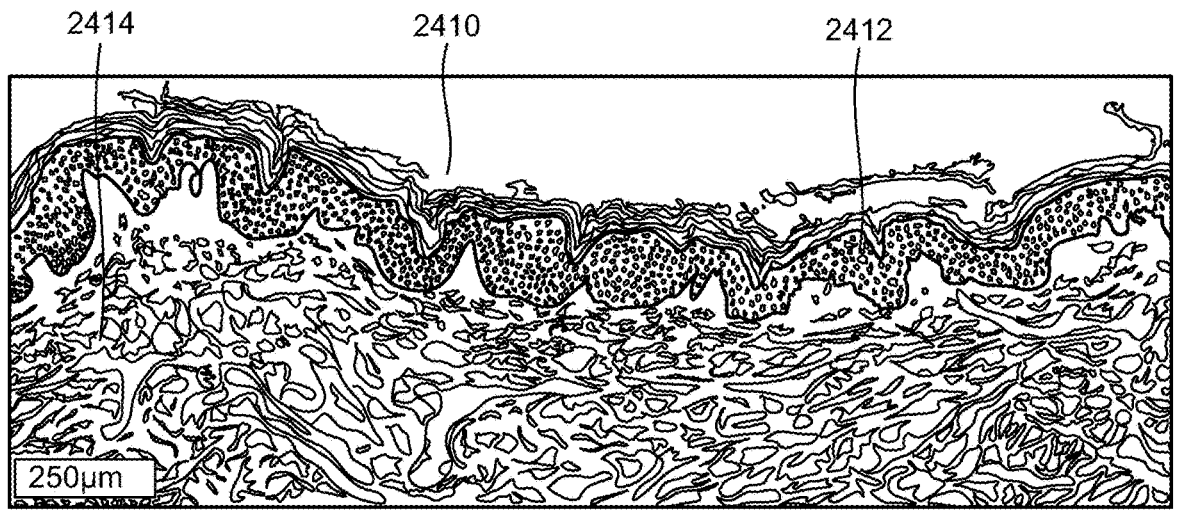
FIG. 24E shows an image of an exemplary histology of a Porcine skin sample taken after ex vivo treatment and stained with Fontana-Mason.
Figure 24F:
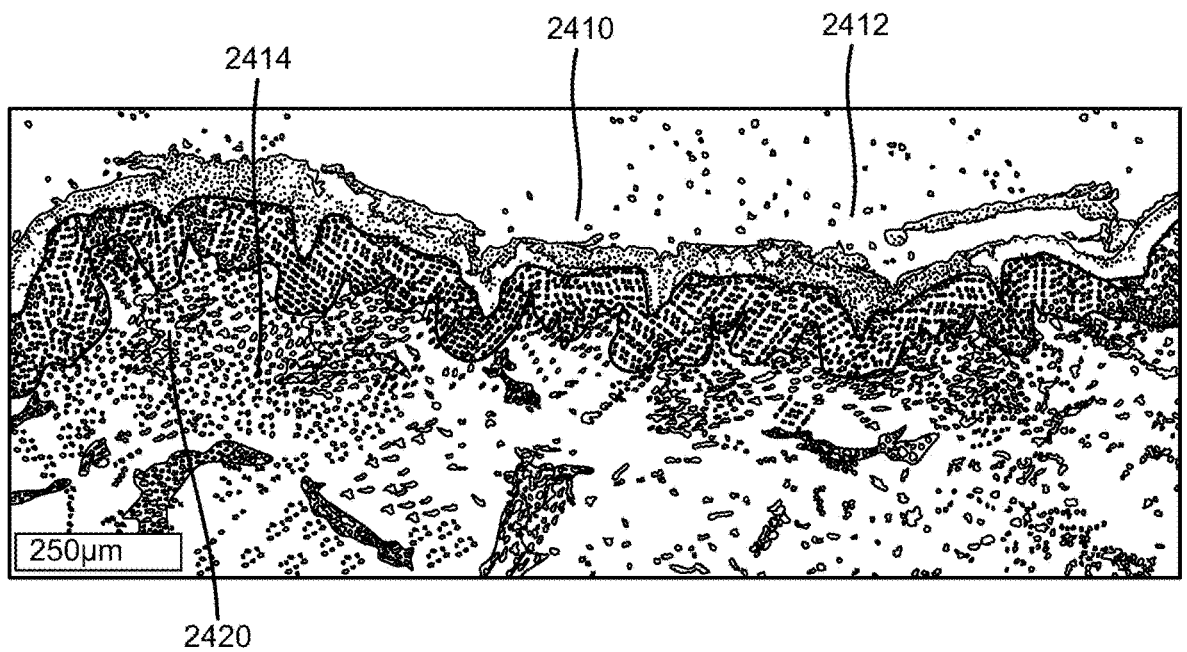
FIG. 24F shows an image of an exemplary histology of a Porcine skin sample taken after ex vivo treatment and stained with TUNEL.
Figure 24G:
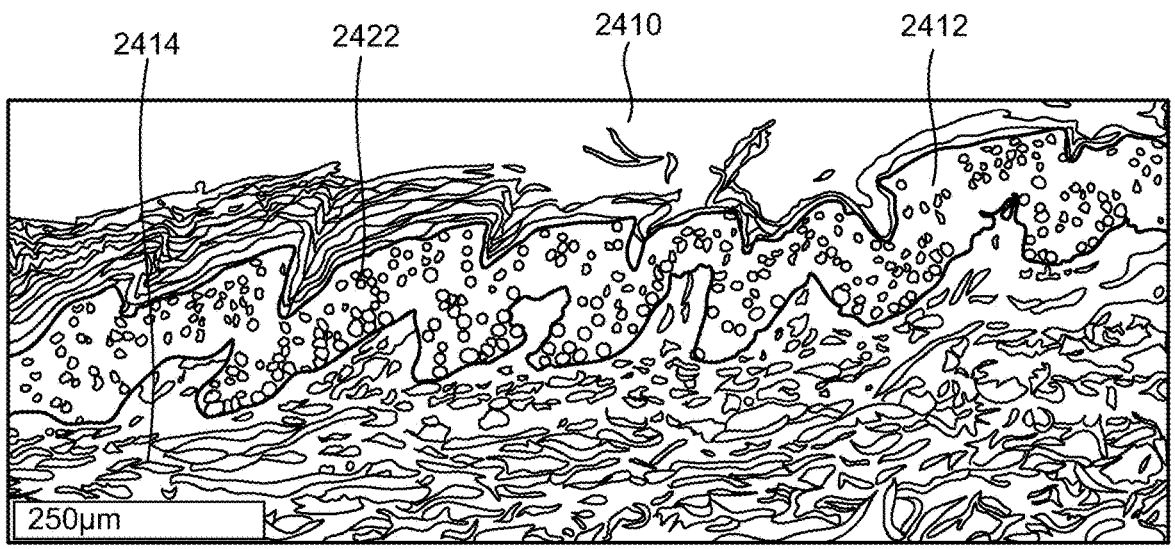
FIG. 24G shows an image of an exemplary histology of a Porcine skin sample taken after ex vivo treatment and stained with Fontana-Mason.
Figure 24H:
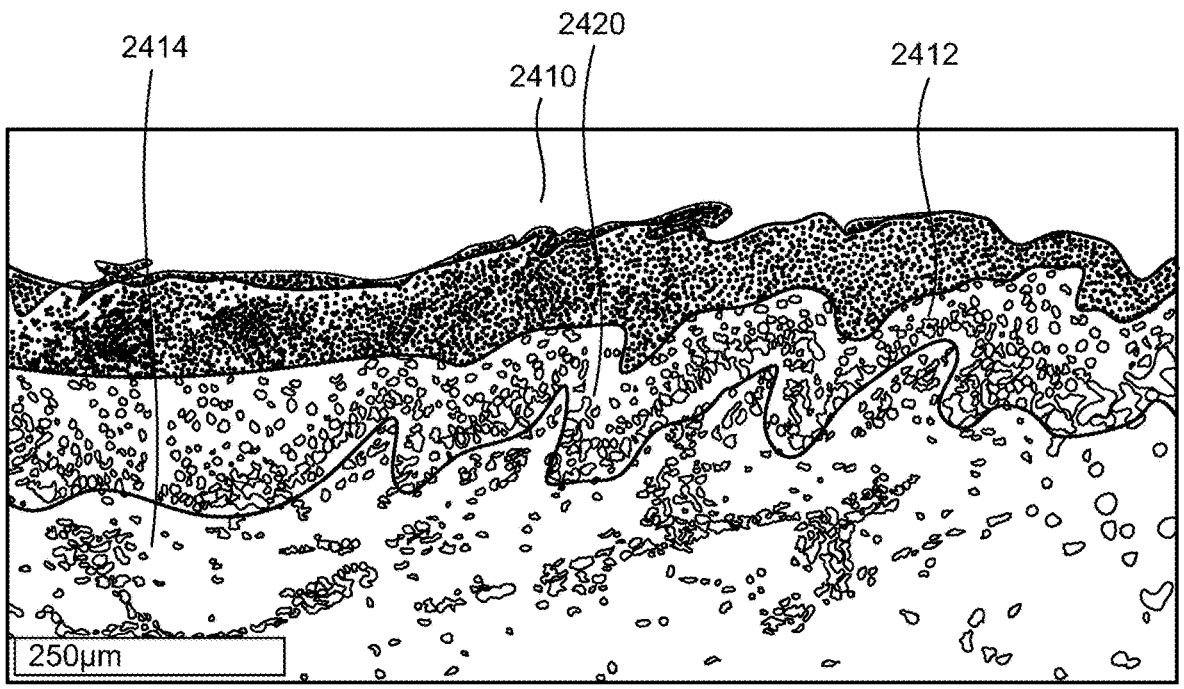
FIG. 24H shows an image of an exemplary histology of a Porcine skin sample taken after ex vivo treatment and stained with TUNEL.

Biopsies from SAMPLES 1-4 were taken and histologies were performed. Representative images of these histologies are shown in FIGS. 24A-H. FIGS. 24A-B show a Fontana-Mason (FM) stain and a TUNEL stain of control SAMPLE 4. FIGS. 24C-D show an FM stain and a TUNEL stain of SAMPLE 1. FIGS. 24E-F show an FM stain and a TUNEL stain of SAMPLE 2. FIGS. 24G-H show an FM stain and a TUNEL stain of SAMPLE 3. Fontan-Mason stains dark in presence of pigment, such as melanin. TUNEL fluoresces in presence of apoptosis (or scheduled cell death).

Referring to FIG. 24A, the control SAMPLE 4 is shown to have a stratum corneum layer 2410, an epidermal layer 2412, and a dermal layer 2414. Undisrupted melanin containing cells 2416 are shown at the bottom of the epidermis 2412. Comparatively little fluorescence is shown in FIG. 24B illustrating a presence of relatively few apoptotic cells.

Histologies of SAMPLE 1 are shown in FIGS. 24C-D. Some disruption appears present in the epidermal layer as evidenced by small vacuoles 2418 shown in FIG. 24C. Additionally, more fluorescence is present in the TUNEL staining of SAMPLE 1 than the control indicating more apoptotic cells 2420. Treatment for SAMPLE 1 was directed to a focal depth of approximately 200 micrometers beneath the surface of the skin and plasma was visible during treatment.

Histologies of SAMPLE 2 are shown in FIGS. 24E-F. Comparatively, little disruption is shown in the epidermal layer 2412 in FIG. 24E. FIG. 24F shows some fluorescence, especially in the dermis 2414 indicating apoptotic cells 2420. Treatment for SAMPLE 2 was directed to a focal depth of approximately 830 micrometers beneath the surface of the skin and no plasma was visible during treatment.

Histologies of SAMPLE 3 are shown in FIGS. 24G-H. A relatively large amount of disruption is shown in the epidermal layer 2412, as indicated by large vacuoles 2422 in FIG. 24G. FIG. 24H shows some fluorescence indicating some apoptotic cells 2420 about the vacuoles 2422. Treatment for SAMPLE 3 was the most superficial being directed to a focal depth of approximately 130 micrometers beneath the surface of the skin and plasma was visible during the treatment.

Methods of treating various skin conditions, such as for cosmetic purposes, can be carried out using the systems described herein. It is understood that although such methods can be conducted by a physician, non-physicians, such as aestheticians and other suitably trained personnel may use the systems described herein to treat various skin conditions with and without the supervision of a physician.

Certain exemplary embodiments have been described to provide an overall understanding of the principles of the structure, function, manufacture, and use of the systems, devices, and methods disclosed herein. One or more examples of these embodiments have been illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Additional Embodiments

In some embodiments, the repetition rate of the input laser beam can be faster than the decay rate of the plasma in the target tissue/target material. This can allow for continuous (e.g., temporally continuous, spatially continuous, etc.) generation of plasma. The area of the treatment region/target region (e.g., region in which plasma is generated) can be controlled by changing the repetition rate of the laser beam.

One skilled in the art will appreciate further features and advantages based on the above-described embodiments. Accordingly, embodiments of the disclosure are not to be limited by what has been particularly shown and described, except as indicated by the appended claims. All publications and references cited herein are expressly incorporated herein by reference in their entirety.

What is claimed is:

1. A method comprising:
   receiving, by a first diffractive optical element, a singe user beam;
   generating, by the first diffractive optical element, a plurality of primary beams from the single laser beam;
   receiving, by a second diffractive optical element, the plurality of primary beams;
   generating, by the second diffractive optical element, a first secondary beam and a second secondary beam from at least a first primary beam of the plurality of primary beams; and
   focusing the first secondary beam to a first focal region in a target tissue and the second secondary beam to a second focal region in the target tissue, wherein the first focal region is located at a first depth from a surface of the target tissue, and the second focal region is located at a second depth different from the first depth of the surface of the target tissue.

2. The method of claim 1, wherein the first secondary beam is configured to generate a first plasma in the first focal region and the second secondary beam is configured to generate a second plasma in the second focal region.

3. The method of claim 1, wherein the first focal region overlaps the second focal region.

4. The method of claim 3, further comprising:
   generating from a second primary beam of the plurality of primary beams, a third secondary beam and a fourth secondary beam;
   focusing the third secondary beam to a third focal region and the fourth secondary beam to a fourth focal region in the target tissue.

5. The method of claim 4, wherein the third secondary beam is configured to generate plasma in the third focal region and the fourth secondary beam is configured to generate plasma in the fourth focal region.

6. The method of claim 5, further comprising distorting the surface of the target tissue to locate the third focal region at the first depth from the surface of the target tissue and the fourth focal region at the second depth from the surface of the target tissue.

7. The method of claim 4, wherein the first and the second secondary beams are focused by a first lens of a multi-lens array, and the third and the fourth secondary beams are focused by a second lens of the multi-lens array.

8. The method of claim 4, wherein the first, the second, the third and the fourth secondary beams are focused by an objective.

9. The method of claim 1, wherein the first diffractive optical element is a diffractive beam splitter.

10. The method of claim 1, wherein an optical element having numerical aperture between about 0.3 and about 1 focuses the first secondary beam to the first focal region.

11. The method of claim 2, wherein the generated first plasma is configured to produce a thermal damage at the first focal region in the target tissue, the thermal damage extending from about the first depth to about the second depth.

12. The method of claim 2, wherein the first secondary beam is configured to selectively generate plasma in a volume that includes a target in the quasi-diffraction-free focal region.

13. A system comprising:
   a diffractive beam splitter configured to receive a single laser beam and produce a plurality of primary beams;
   a diffractive element located down-beam from the diffractive beam splitter, the diffractive element configured to receive at least a first primary beam of the plurality of primary beams and generate at least a first secondary beam and a second secondary beam; and
   a focusing element located down-beam from the diffractive element, the focusing element being configured to focus the first secondary beam to a first focal region in a target tissue and focus the second secondary beam to a second focal region in the target tissue, wherein the first focal region is located at a first depth from a surface of the target tissue, and the second focal region is located at a second depth different from the first depth of the surface of the target tissue.

14. The system of claim 13, wherein the first secondary beam and the second secondary beam are generated by a first Fresnel zone plate in an array of Fresnel zone plates.

15. The system of claim 14, wherein the diffractive element is configured to:
   receive a second primary beam of the plurality of primary beams and generate at least a third secondary beam and a fourth secondary beam; and
   focus the third secondary beam to a third focal region and the fourth secondary beam to a fourth focal region in the target tissue.

16. The system of claim 15, wherein the third secondary beam is configured to generate plasma in the third focal region and the fourth secondary beam is configured to generate plasma in the fourth focal region.

17. The system of claim 15, wherein the first and the second secondary beams are focused by a first lens of a multi-lens array, and the third and the fourth secondary beams are focused by a second lens of the multi-lens array.

18. The method of claim 1, wherein the first secondary beam and the second secondary beam have different divergences.

19. The method of claim 18, wherein the second diffractive optical element is configured to distribute the intensity of the first primary beam in a selected proportion between the first secondary beam and the second secondary beam.

* * * * *